(12) United States Patent
Green et al.

(10) Patent No.: US 11,672,777 B2
(45) Date of Patent: *Jun. 13, 2023

(54) TERPENE-BASED COMPOSITIONS, METHODS OF PREPARATIONS AND USES THEREOF

(71) Applicant: ELEVATE TECHNOLOGIES LLC, San Juan, PR (US)

(72) Inventors: Wayne Green, Encinitas, CA (US); Shea Alderete, San Clemente, CA (US); Justin Freyre, Encinitas, CA (US)

(73) Assignee: Elevate Technologies LLC, San Juan, PR (US)

( * ) Notice: Subject to any disclaimer, the term of this patent is extended or adjusted under 35 U.S.C. 154(b) by 118 days.

This patent is subject to a terminal disclaimer.

(21) Appl. No.: 16/895,214

(22) Filed: Jun. 8, 2020

(65) Prior Publication Data
US 2020/0316015 A1 Oct. 8, 2020

Related U.S. Application Data

(63) Continuation of application No. 15/889,112, filed on Feb. 5, 2018, now Pat. No. 10,675,264.

(Continued)

(51) Int. Cl.
*A61K 36/00* (2006.01)
*A61K 31/352* (2006.01)
(Continued)

(52) U.S. Cl.
CPC ............ *A61K 31/352* (2013.01); *A61K 31/01* (2013.01); *A61K 31/015* (2013.01);
(Continued)

(58) Field of Classification Search
CPC ...................................................... A61K 36/00
See application file for complete search history.

(56) References Cited

U.S. PATENT DOCUMENTS

2006/0222723 A1 10/2006 Bevilacqua
2014/0271940 A1 9/2014 Wurzer
(Continued)

FOREIGN PATENT DOCUMENTS

WO WO 2016-103254 A1 6/2016
WO WO 2016-123160 A1 8/2016
WO WO 2016-199148 A1 12/2016

OTHER PUBLICATIONS

Kratzeisen et al., "Influence of free fatty acid content of coconut oil on deposit and performance of plant oil pressure stoves," Fuel 89:1583-1589, 2010.*
(Continued)

*Primary Examiner* — Rosanne Kosson
(74) *Attorney, Agent, or Firm* — Knobbe, Martens, Olson & Bear, LLP

(57) ABSTRACT

The present disclosure generally relates to terpene-based compositions for applications in the pharmaceutical and recreational fields. In some embodiments, the compositions are enriched compositions or non-naturally occurring compositions which contain defined concentrations of one or more *cannabis*-derived chemical compounds, such as terpenes and cannabinoids that have a distinctive characteristic that mimics that of a *cannabis* plant matter or a product thereof. Also provided in some embodiments of the disclosure are methods for the preparation of the compositions, as well as methods for use thereof.

27 Claims, 12 Drawing Sheets

Related U.S. Application Data

(60) Provisional application No. 62/456,047, filed on Feb. 7, 2017.

(51) Int. Cl.

| | | |
|---|---|---|
| *C12Q 1/6895* | (2018.01) | |
| *A61K 31/01* | (2006.01) | |
| *A61K 31/015* | (2006.01) | |
| *A61P 25/00* | (2006.01) | |
| *A61K 31/192* | (2006.01) | |
| *A61K 31/045* | (2006.01) | |
| *A61K 36/185* | (2006.01) | |
| *C11B 9/00* | (2006.01) | |
| *C12Q 1/6827* | (2018.01) | |

(52) U.S. Cl.
CPC .......... *A61K 31/045* (2013.01); *A61K 31/192* (2013.01); *A61K 36/185* (2013.01); *A61P 25/00* (2018.01); *C11B 9/00* (2013.01); *C12Q 1/6827* (2013.01); *C12Q 1/6895* (2013.01); *C12Q 2600/156* (2013.01)

(56) References Cited

U.S. PATENT DOCUMENTS

2017/0021029 A1\* 1/2017 Raber ................. A61K 9/12
2018/0193403 A1\* 7/2018 George ................. A23L 33/115

OTHER PUBLICATIONS

International Search Report and Written Opinion for PCT/US2018/016913 dated Jun. 8, 2018.
Andrea et al., "Analysis of some Italian lemon liquors (limoncello)", J. Agric. Food Chem. 51:4978-4983, 2003.
Dagulo et al., "Chemical Characterization of Orange Juice from Trees Infected with Citrus Greening (Huanglongbing)", J. Food Sci. 75:0199-207, 2010.
Diego et al., "Aromatherapy positively affects mood, EEG patterns of alertness and math computations", (1998) Int. J. Neurosci. 96:217-224.
El-Alfy et al., "Antidepressant-like effect of delta9-tetrahydrocannabinol and other cannabinoids isolated from *Cannabis sativa* L", 2010, Pharmacology Biochemistry and Behavior 95 (4): 434-42.
Hendriks and Bruins, "A Tentative Identification of Components in the essential Oil of *Cannabis sativa* L. by a Combination of Gas Chromatography Negative Ion Chemical Ionization Mass Spectrometry and Retention Indices", Biol. Mass Spectrom. 10:377-381, 1983.
Heuberger et al., "Transdermal absorption of (-)-linalool induces autonomic deactivation but has no impacton ratings of well-being in humans", Neuropsychopharmacology. 29:1925-1932, 2004.
Jella et al., "Determination of Key Flavor Components in Methylene Chloride Extracts from Processed Grapefruit Juice", J. Agric. Food Chem. 46:242-247, 1998.
Knasko, "Ambient odor's effect on creativity, mood, and perceived health", (1992) Chem. Senses. 17;27-35.
Mucci et al., "Citron and lemon under the lens of HR-MAS NMR spectroscopy", Food Chem. 141:3167-3176, 2013.
Musenga et al., "Simultaneous determination of aromatic and terpenic constituents of cloves by means of HPLC with diode array detection", J. Sep. Sci. 29:1251-1258, 2006.
Reineccius TA et al., "Flavor Release from Cyclodextrin Complexes: Comparison of Alpha, Beta, and Gamma Types", Journal of Food Science, 68(4), 1234-1239, 2003.
Rubiano et al., "Encapsulation of d-limonene flavors using spray drying: Effect of the addition of emulsifiers", Ing. Compel, vol. 17 No. 2 Cali 2015.
Satoh and Sugawara, "Effects on Humans Elicited by Inhaling the Fragrance of Essential Oils: Sensory Test, Multi-Channel Thermometric Study and Forehead Surface Potential Wave Measurement on Basil and Peppermint", Analytical Sciences. 19:139-146, 2003.
Scalarone et al., "MALDI-TOF mass spectrometry on cellulosic surfaces of fresh and photo-aged di- and triterpenoid varnish resins", J. Mass Spectrom. 40:1527-1535, 2005.
Sugawara et al., "Perceived Fragrance of Essential Oils in Relation to Type of Work", J. Home Econ. Jpn. 49:1281-1290, 1998.
Sugawara et al., "Relationship between Mood Change, Odour and Its Physiological Effects in Humans While Inhaling the Fragrances of Essential Oils as Well as Linalool and Its Enantiomers", Molecules. 18:3312-3338, 2013.
Trofin, I. G. et al., "Identification and Characterization of Special Types of Herbal Cannabis", U.P.B. Sci. Bull., Series B, vol. 74, Iss. 1, 2012, pp. 119-130.
Villa et al., "High-performance liquid chromatographic method for the simultaneous determination of 24 fragrance allergens to study scented products", J. Pharm. Biomed. Anal. 44:755-762, 2007.
Yamamoto et al., "Molecular encapsulation of citral or d-limonene flavor by spray drying", Proceedings of the 11th International Congress on Engineering and Food. 7-8.
Yang et al., "Caryophyllenes from a Fungal Culture of *Chrysosporiumpilosum*", J. Nat. Prod. 72:484-487, 2009.
Zhang et al., "Studies on cytotoxic triterpene saponins from the leaves of *Aralia elata*", Food Chem. 138:208-213, 2013.

\* cited by examiner

TERPENE-BASED COMPOSITIONS, METHODS OF PREPARATIONS AND USES THEREOF

CROSS-REFERENCE TO RELATED APPLICATIONS

The present application is a continuation of U.S. patent application Ser. No. 15/889,112, filed Feb. 5, 2018, now U.S. Pat. No. 10,675,264, which claims priority to U.S. Provisional Application Ser. No. 62/456,047, filed on Feb. 7, 2017, the disclosure of each of which is incorporated herein by reference in its entirety.

INCORPORATION OF THE SEQUENCE LISTING

The material in the accompanying sequence listing is hereby incorporated by reference into this application. The accompanying sequence listing text file, named WGREE-001A_Sequence_Listing.txt, was created on Feb. 5, 2018 and is 70 KB. The file can be assessed using Microsoft Word on a computer that uses Windows OS.

FIELD

Some embodiments relate to compositions for imparting one or more desired effects to a subject in which a plurality of chemical compounds which are known to occur in a *cannabis* strain and are associated with at least one desired effect in a subject are enriched and wherein the amounts or levels of the plurality of chemical compounds with respect to one another in said composition are about the amounts or levels of the plurality of chemical compounds with respect to one another in said *cannabis* strain. Some embodiments relate to terpene-based compositions for applications in the pharmaceutical and recreational fields. Also provided in some embodiments of the disclosure are methods for the preparation of the compositions, as well as methods for use thereof.

BACKGROUND

*Cannabis* is a genus of the flowering plant *Cannabis* which has long been used for drug and industrial purposes, fiber (hemp), for seed and seed oils, for medicinal purposes, and as a recreational drug. Industrial hemp products are made from *Cannabis* plants selected to produce an abundance of fiber. The *Cannabis* plant is an annual, dioecious, flowering herb indigenous to central Asia and the Indian subcontinent. The *Cannabis* plant material has been reported to contain suitable and desirable compounds, useful in various pharmaceutical dosage forms and methods of medical treatment. Cannabinoids, terpenoids, and flavonoids are included amongst the various suitable and desirable compounds.

The medicinal and psychoactive properties of the *Cannabis* plant have been documented for centuries. Growing evidence suggests that *Cannabis* is a safe, versatile and potentially inexpensive drug. It has been reported as being beneficial to patients suffering from a wide range of symptoms experienced in connection with various, often very serious, medical conditions. For example, *Cannabis* has been reported as being useful to alleviate symptoms associated with cancer, anorexia, chronic pain, spasticity, arthritis, migraine and many other illnesses. As a result, recent research into the use of *cannabis*-derived products for the treatment of a variety of diseases and conditions is reaching a feverish pace. In the United States, *Cannabis* has become an important, emerging medical option in a number of states. It is quickly becoming clear that drug formulations containing specific *cannabis*-derived chemical compounds can have dramatic affect in improving the lives of many patients. This extends well past the treatment of nausea, glaucoma, or pain relief which has been traditionally treated with *cannabis* as a "shotgun" approach. It has become clear that the use of targeted *cannabis*-derived chemical compounds for a specific ailment is much more effective.

The physiological and pharmacological effects of *cannabis*-derived products depend upon a number of factors, including the dosage level and the route of administration. In *Cannabis*, the content and composition of terpenes are strongly inherited and therefore have been widely used as biochemical markers in chemo-systematic studies to characterize plant species, provenances, clones and hybrids thereof. *Cannabis* plants can exhibit wide variation in the quantity and type of chemical compounds that they produce. In fact, a wide variability in terpenes, terpenoids, and/or cannabinoids content in different strains of *Cannabis* has been reported. In addition, as is also the case for many other plant species, *Cannabis* plants often exhibit dynamic biochemical changes when attacked by diseases and herbivores and in response to abiotic stresses, resulting in the induced production and release of aroma volatiles that are beneficial for direct or indirect defense. As a result, plant materials harvested from *cannabis* plants and products derived therefrom typically exhibit great variations in their chemical composition and quality.

Therefore, there is growing need for compositions, systems, and methods for the preparation of drug product formulations, for both medicinal and recreational use, in large quantity and with more consistent quality.

SUMMARY

This section provides a general summary of the present application, and is not comprehensive of its full scope or all of its features.

In one aspect, some embodiments disclosed herein relate to method of making a composition for imparting one or more desired effects to a subject. The method includes preparing a composition in which a plurality of chemical compounds which are known to occur in a *cannabis* strain and are associated with at least one desired effect in a subject are enriched, wherein the amounts or levels of the plurality of chemical compounds with respect to one another in the composition are about the amounts or levels of the plurality of chemical compounds with respect to one another in the *cannabis* strain.

Implementations of embodiments of the method according to this aspect and other aspects of the present disclosure can include one or more of the following features. In some embodiments, the preparation of the composition includes (i) obtaining a first enriched or purified composition of a first chemical compound from among the plurality of chemical compounds associated with at least one desired effect in a subject and which is known to occur in a *cannabis* strain, and (ii) combining the first enriched or purified composition with a second enriched or purified composition of a second chemical compound from among the plurality of chemical compounds associated with at least one desired effect in a subject and which is known to occur in the *cannabis* strain. In some embodiments, the plurality of chemical compounds are selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements. In some embodiments, the plurality of chemical compounds includes at least one terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds includes at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the plurality of chemical compounds includes at least one terpene compound selected from the group consisting of caryophyllene, limonene, linalool, myrcene, α-pinene, and β-pinene.

In some embodiments disclosed herein, the amounts or levels of the plurality of chemical compounds relative to one another in the composition are about the amounts or levels of the plurality of chemical compounds relative to one another in a *cannabis* strain selected from FIGS. 1-12. In some embodiments, the total amount of terpenes in the composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume.

In some embodiments of the present disclosure, the composition further includes an essential oil. In some embodiments, the essential is lime oil. In some particular embodiments, the final concentration of essential oil in the composition is at least about 0.1%, at least about 0.2%, at least about 0.5%, at least about 1%, at least about 2%, at least about 3%, at least about 4%, at least about 5%, or at least about 10% by volume. In yet some embodiments, the final concentration of essential oil in the composition is from about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume.

In some embodiments disclosed herein, the plurality of chemical compounds includes one or more cannabinoid compound. In some embodiments, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume.

In some embodiments of the present disclosure, the composition further includes a medium-chain fatty acid triester of glycerol, which is also known as medium-chain triglyceride—MCT. In some embodiments, the MCT includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the ratio of the MCT amount to the amount of the at least one terpene compound is from about 1:1000 to about 1000:1 by volume. In some embodiments, the ratio of the MCT amount to the amount of the at least one terpene compound is about 100:1 to about 3:1 by volume.

In some embodiments disclosed herein, the *cannabis* strain is a hybrid *cannabis* strain or an inbred *cannabis* strain. In some embodiments, the *cannabis* strain is a strain of *Cannabis sativa, Cannabis indica,* or *Cannabis ruderalis*. In some embodiments, the *cannabis* strain is a *cannabis* strain selected from the group consisting of ACDC PX, AG1 Lemon, AG2 Orange, Bluebbery OG, Jet Fuel, Kalashnikova, Keep Tahoe OG, Pineapple Xpress, Sour AK, Strawberry AK, Terpin Gorilla, and Watermelon OG. In some embodiments, a representative seed sample of the *cannabis* strain has been deposited under NCIMB Nos. 41541, 42254, 42255, 42256, 42257, and 42258.

In one aspect, some embodiments disclosed herein relate to a method for characterizing a *cannabis* strain, which includes identifying one or more genetic characteristics present in a biological sample from the *cannabis* strain wherein the one or more genetic characteristics are associated with a desired level or amount of one or more chemical compounds in the *cannabis* strain which is associated with at least one desired effect in a subject. In some embodiments, the method includes determining a plurality of genetic characteristics in a biological sample from the *cannabis* strain. In some embodiments, the plurality of genetic characteristics includes at least 2, at least 5, at least 10, at least 15, at least 20, at least 25, at least 50, or at least 100 genetic characteristics. In some embodiments, the plurality of genetic characteristics in the biological sample includes: (i) at least one molecular genetic marker selected from the group consisting of a simple sequence repeat (SSR), a cleaved amplified polymorphic sequence (CAPS), a simple sequence length polymorphism (SSLP), a restriction fragment length polymorphism (RFLP), a random amplified polymorphic DNA (RAPD) marker, a single nucleotide polymorphism (SNP), an amplified fragment length polymorphism (AFLP), an insertion, a deletion, an InDel mutation, an epigenetic alteration, a splicing variant, and a haplotype created from two or more of the above described molecular genetic marker; or (ii) at least one molecular genetic marker in conjunction with one or more phenotypic measurements, microarray data, analytical measurements (e.g., an RNA/protein overexpression, and an aberrant RNA/protein expression), biochemical measurements, environmental measurements, or transcription levels. In some embodiments, the identification of one or more genetic characteristics in the biological sample includes performing an analytical assay selected from the group consisting of nucleic acid sequencing, polypeptide sequencing, restriction digestion, nucleic acid amplification-based assays, nucleic acid hybridization assay, capillary electrophoresis, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), in-silico comparative genomics, and an enzymatic activity assay. In some embodiments, the identification of the one or more genetic characteristics in the biological sample comprises an antibody-based assay selected form the group consisting of ELISA, immunohistochemistry, western blotting, mass spectrometry, flow cytometry, protein-microarray, immunofluorescence, and a multiplex detection assay. In some embodiments, the one or more genetic characteristics in the biological sample is selected from the genetic characteristics described by Bakel et al. (supra, 2011)

In some embodiments, the method according to this aspect and other aspects of the present disclosure includes determining a plurality of genetic characteristics associated with a desired level or amount of a plurality of chemical compounds in the *cannabis* strain. In some embodiments, the plurality of chemical compounds includes at least 2, at least 3, at least 4, at least 5, at least 10, at least 15, at least 20, at least 25, at least 30, at least 35, or at least 40 chemical compounds.

In one aspect, some embodiments disclosed herein relate to a method of determining a profile of the amounts or levels of a plurality of chemical compounds associated with at least one desired effect in a subject, the method includes (i) obtaining a *cannabis* plant sample including the plurality chemical compounds, and (ii) determining the amounts or levels of the plurality chemical compounds in the *cannabis* plant sample.

In some embodiments of the methods disclosed herein, the determination of the level or amount of the plurality of chemical compounds includes an analytical assay selected from gas chromatography (GC), flame ionization detector (FID), thin layer chromatography (TLC) analysis, and high performance liquid chromatography (HPLC).

In one aspect, some embodiments disclosed herein relate to a composition for imparting one or more desired effects to a subject, wherein a plurality of chemical compounds which are known to occur in a *cannabis* strain and are associated with at least one desired effect in a subject are enriched in the composition and wherein the amounts or levels of the plurality of chemical compounds with respect to one another in the composition are about the amounts or levels of the plurality of chemical compounds with respect to one another in the *cannabis* strain. Implementations of embodiments of the composition according to this aspect and other aspects of the disclosure can include one or more of the following features. In some embodiments, the composition includes (i) a first enriched or purified composition of a first chemical compound from among the plurality of chemical compounds associated with at least one desired effect in a subject and which is known to occur in a *cannabis* strain, and (ii) a second enriched or purified composition of a second chemical compound from among the plurality of chemical compounds associated with at least one desired effect in a subject and which is known to occur in the *cannabis* strain. In some embodiments, the plurality of chemical compounds includes at least one terpene compound selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other element. In some embodiments, the plurality of chemical compounds includes at least one terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds includes at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the plurality of chemical compounds includes at least one terpene compound selected from the group consisting of caryophyllene, limonene, linalool, myrcene, α-pinene, and β-pinene. In some embodiments, the amounts or levels of the plurality of chemical compounds relative to one another in the composition are about the amounts or levels of the plurality of chemical compounds relative to one another in a *cannabis* strain selected from FIGS. 1-12. In some embodiments, the total amount of terpenes in the composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume.

In some embodiments disclosed herein, the composition further includes an essential oil. In some embodiments, the essential is lime oil. In some embodiments, the final concentration of essential oil in the composition is at least about 0.1%, at least about 0.2%, at least about 0.5%, at least about 1%, at least about 2%, at least about 3%, at least about 4%, at least about 5%, or at least about 10% by volume. In some embodiments, the final concentration of lime oil in the composition is from about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume.

In some embodiments disclosed herein, the composition further includes one or more cannabinoid compound. In some embodiments, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA) active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA), active analogues and derivatives of any one thereof. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In some embodiments, the composition further comprises a medium-chain fatty acid triester of glycerol (medium-chain triglyceride—MCT). In some embodiments, the MCT includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the ratio of the MCT amount to the amount of the at least one terpene compound is from about 1:1000 to about 1000:1 by volume. In some embodiments, the ratio of the MCT amount to the amount of the at least one terpene compound is from about 100:1 to about 3:1 by volume.

In some embodiments disclosed herein, the *cannabis* strain is a hybrid *cannabis* strain or an inbred *cannabis* strain. In some embodiments, the *cannabis* strain is a strain of *Cannabis sativa, Cannabis indica*, or *Cannabis ruderalis*. In some embodiments, the *cannabis* strain is a *cannabis* strain selected from the group consisting of ACDC PX, Blubbery OG, Jet Fuel, Kalashnikova, Keep Tahoe OG, Pineapple Xpress, Sour AK, Strawberry AK, Terpin Gorilla, and Watermelon OG. In some embodiments, a representative seed sample of the *cannabis* strain has been deposited under NCIMB Nos. 41541, 42254, 42255, 42256, 42257, and 42258.

In one aspect, some embodiments of the present disclosure relate to a non-naturally occurring composition for conferring a desired effect to a subject, the composition including one or more *cannabis* terpene and a medium-chain triglyceride (MCT). In some embodiments, the one or more *cannabis* terpene is selected from the group consisting of monoterpenes, diterpenes, triterpenes, hemiterpenes, sesquiterpenes, sesterterpenes, sesquarterpenes, and notisoprenoids. In some embodiments, the one or more *cannabis* terpene is selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene.

In some embodiments, the non-naturally occurring composition of the present disclosure includes at least two *cannabis* terpenes selected from the group consisting of caryophyllene, myrcene, and α-pinene. In some embodiments, the non-naturally occurring composition further includes one or more additional *cannabis* terpene compounds selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the one or more additional *cannabis* terpene compounds is selected from the group consisting of the one or more terpene compounds are selected from the group consisting of caryophyllene, myrcene, α-pinene, limonene, linalool, and β-pinene.

In some embodiments, the total amount of terpenes in the composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the non-naturally occurring composition of the present disclosure further includes an amount of an essential oil. In some embodiments, the essential oil is lime oil. In some embodiments, the final concentration of essential oil in the composition is at least about 0.1%, at least about 0.2%, at least about 0.5%, at least about 1%, at least about 2%, at least about 3%, at least about 4%, at least about 5%, or at least about 10% by volume. In some embodiments, the final concentration of essential oil in the composition is from about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the non-naturally occurring composition of the present disclosure further includes one or more cannabinoid compound. In some embodiments, the at least one cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In some embodiments, the medium-chain triglyceride (MCT) of the non-naturally occurring composition of the present disclosure includes at least one medium-chain fatty acid having an aliphatic tail of 6-12 carbon atoms. In some embodiments, the at least one medium-chain fatty acid is selected from the group consisting of caproic acid (hexanoic acid), caprylic acid (ocanoic acid), capric acid (decanoic acid), and lauric acid (dodecanoic acid). In some embodiments, the at least one medium-chain fatty acid comprises caprylic acid. In some embodiments, the ratio of the MCT amount to the amount of the one or more cannabis terpene is of from about 1:1000 to 1000:1 by volume. In some embodiments, the ratio of the MCT amount to the amount of the one or more cannabis terpene is of about 100:1 to 3:1 by volume. In some embodiments, the desired effect is selected from the list consisting of reduced anxiety, reduced depression, improved alertness, cognitive ability enhancement, mood improvement, improved sleep quality, nausea reduction, pain relief, spasm relief, seizure decrease, muscle relaxation, antimicrobial, anti-diabetes, blood circulation improvement, psoriasis relief, anti-inflammation, relief of connective tissue disorder, bone stimulation, relief of rheumatoid arthritis, anti-oxidation, improvement to mobility (e.g., arthritis, multiple sclerosis), improvements to skin conditions (e.g., blemishes, scars, insect bites, hives, pimples), reduced seizures (epilepsy), reduction in hypertension, improved memory loss (e.g., dementia, Alzheimer's), reduced dependency on drugs (e.g. opioids, nicotine, alcohol), inhibition of cancer growth, increased metabolism, improvements to autoimmune disorders, appetite stimulation, reduced concussive injuries, and enhancement of skin penetration for transdermal delivery of therapeutic drug.

In some embodiments, the composition of the present disclosure is further formulated for administration orally, transdermally, topically, or parenterally. In some embodiments, the composition the present disclosure is further formulated into a form selected from a tablet, a vaporizer inhalant, a capsule, a gel, a power, an oral spray, a chewable gum, a sublingual film or lozenge, and a transdermal patch.

The foregoing summary is illustrative only and is not intended to be in any way limiting. In addition to the illustrative embodiments and features described herein, further aspects, embodiments, objects and features of the application will become fully apparent from the drawings and the detailed description and the claims.

DETAILED DESCRIPTION

Figure 1:
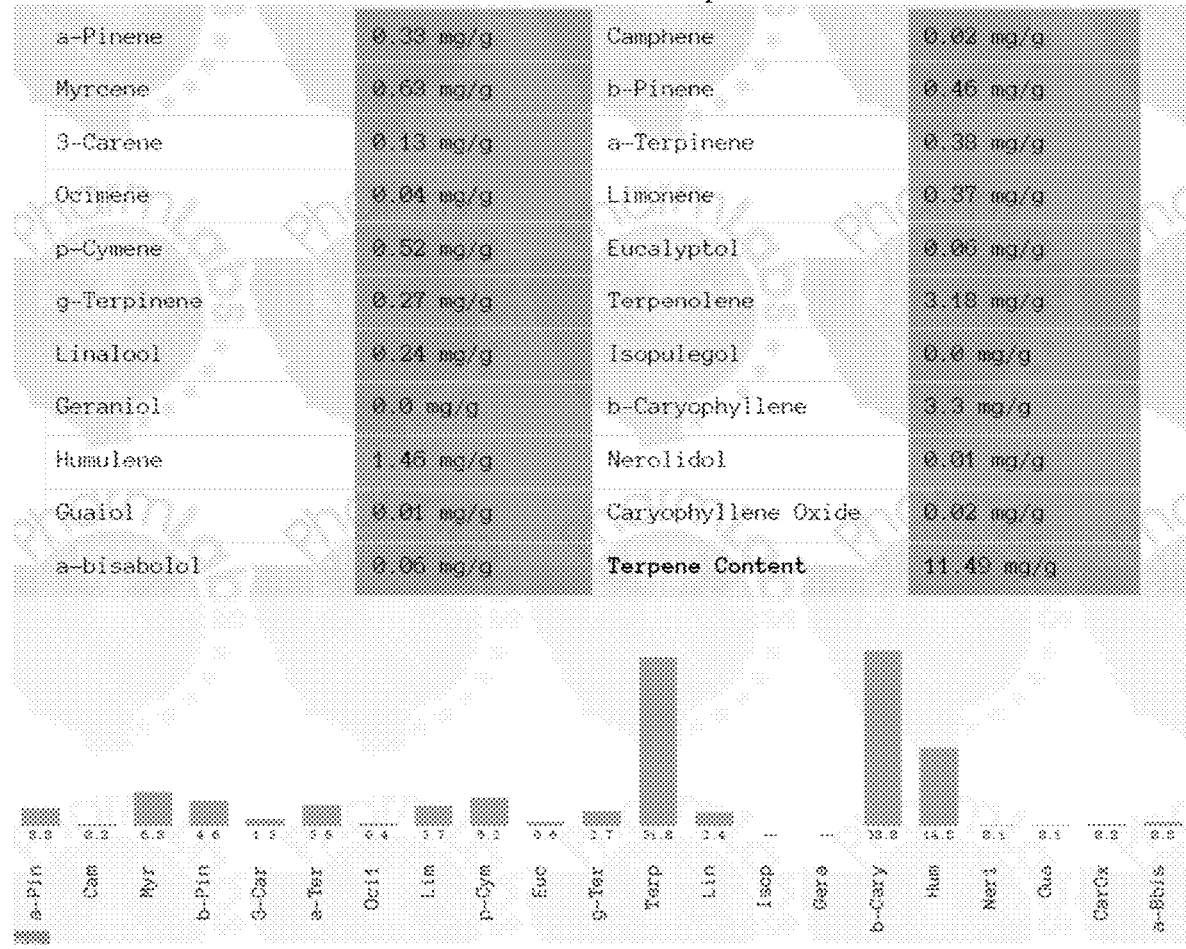
FIG. 1 illustrates an exemplary terpene profile of a plant sample derived from flower tissues of the *cannabis* strain "AG1 Lemon." The specific amounts of each of the terpene compounds present in the sample and the total terpene content are indicated.

The present disclosure generally relates to methods and compositions including one or more chemical compounds which are known to occur in a *Cannabis* plant. Some embodiments disclosed herein relate to enriched formulations that are biomimetic to the aroma, flavor, and pharmaceutical effect of various biochemicals naturally present in particular strains of the *Cannabis* plant, including terpenes and cannabinoids. In some embodiments, these chemical compounds are formulated with one or more fatty acids in order to enhance the bioavailability of the chemical compounds in the resulting formulations in humans, animals, and other biological systems. In some embodiments, these enriched formulations are prepared by recreating the desirable effects of existing *Cannabis* strains, based on knowledge acquired using genomic and/or analytical chemistry techniques. The precursors to the resulting formulations may be, for example, chemical extracts of the *Cannabis* plant or natural or synthetic versions of the chemicals present in *Cannabis*. One main function of these enriched formulations can be to replace the synergistic effects of *Cannabis* compounds when such effects would be lost in the extraction of cannabinoids from *Cannabis*. In some embodiments, the enriched formulations of the disclosure are prepared with the desired *Cannabis* compounds and one or more medium-chain fatty acid triester of glycerol, which is also known as medium-chain triglyceride—MCT, to provide enhanced bioavailability in the human body. For example, in some embodiments, the synergistic interaction between terpenes and cannabinoids, at times referred to as the "Entourage Effect", in the human body is preserved with the addition of formulations discussed in this disclosure. The synergy provides the user a more holistic experience whether utilized for recreational or medicinal purposes. As discussed further below, several formulations disclosed herein have been reported to relieve certain ailments in patients, such as anxiety in PTSD patients.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this disclosure.

References in the following detailed description to "one embodiment," "an embodiment," "an example embodiment," and the like, indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms "administration" and "administering", as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof.

A "bioavailability enhancer" as used herein is an agent or combination of agents that enhance the rate and/or extent of absorption of a compound, such as a *Cannabis*-derived compound, that reaches the systemic circulation and is available at the site of action. A bioavailability enhancer may also improve tissue distribution and targeting of the compound. Examples of bioavailability enhancers include, but are not limited to, liposomes, vitamin E, TPGS (d-α-tocopheryl polyethylene glycol 1000 succinate); acetylated monoglycerides; mono-, di-, and triglyceride esters of medium-chain (6-12 carbon atoms in length) and long-chain (more than 12 carbon atoms in length) fatty acids; esters of fatty acids and glycols or glycerol; esters of mixed fatty acids and glycols or glycerol; diesters of propylene glycol having from about 7 to about 55 carbon atoms; propylene glycol esters of capric and caprylic acids; citric acid, malic acid, ascorbic acid, fumarie acid, caproic acid, caprylic acid, cholic acid, glycocholic acid, sodium cholate, sodium lauryl sulfate, palmitoyl carnitin, cyclosporin A, polyoxyethylene/polyoxypropylene copolymers and other soluble polymers, solid lipid nanoparticles, and mixtures thereof. Soluble bioavailability-enhancing polymers to which compounds may be coupled to as targetable carriers or as compounds which are metabolized into a desired *Cannabis* compound include polyvinylpyrrolidone, pyran copolymer, polyhydroxylpropylmethacrylamide-phenoi, polyhydroxyethylasparta-midephenol, or polyethyleneoxide-polylysine substituted with palmitoyl residues. Furthermore, the compounds or drugs may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

As used herein, "concentrate" or "essential oil" refers to a substance obtained by extracting a raw material, using a solvent, wherein the solvent has substantially been removed. In some embodiments, the process of extracting a raw material using a solvent includes a hot solvent extraction. In some embodiments, the process of extracting a raw material using a solvent includes supercritical fluid extraction (SFE), such as, e.g., a fractional supercritical fluid extraction (FSFE).

As such, the term "*Cannabis* concentrate" or "*Cannabis* essential oil" refers to a substance obtained by extracting *Cannabis* (or any part thereof), wherein the solvent has substantially been removed. The *Cannabis* concentrate can be further enriched with certain desired products (e.g., cannabinoids, terpenoids, and/or flavonoids) from the *Cannabis* plant material.

As used herein, the term "cultivar" refers to a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

As used herein, "enrich" refers to an increase the concentration or amount of one substance, relative to the concentration or amount of another substance; or one material containing a higher concentration or amount of a substance, compared to a second material's concentration or amount of that substance. For example, in some embodiments, an a composition enriched for a *Cannabis* compound may have a higher concentration or amount of the compound relative to the concentration or amount of the compound in the *Cannabis* strain in which the compound is present. The increase in the amount (weight/mass) can be at least about 1%, at least about 5%, at least about 10%, at least about 25%, or at least about 50%. Likewise, the increase in concentration can be at least about 1%, at least about 5%, at least about 10%, at least about 25%, or at least about 50%. In reference to "higher concentration" and "lower concentration," the difference in concentration can be at least about 1%, at least about 5%, at least about 10%, at least about 25%, or at least about 50%.

"Entourage compound" is a compound that can increase the effects of one or more naturally-occurring ligands that bind to one or more receptors, but that has little or no affinity for the receptor. In a preferred, but non-limiting embodiment, an entourage compound increases the effects of a naturally-occurring ligand that binds to one or more cannabinoid receptors, but the entourage compound has little or no affinity for the cannabinoid receptor.

As used herein, "extract" refers to a composition obtained by extracting a raw material, using a solvent system. The term "extract of *Cannabis*" refers to a composition obtained by extracting *Cannabis* (or any part thereof). In some embodiments, the process of extracting a raw material using a solvent includes a hot solvent extraction. In some embodiments, the process of extracting a raw material using a solvent includes supercritical fluid extraction (SFE), such as, e.g., a fractional supercritical fluid extraction (FSFE). In reference to *Cannabis*, suitable extracts include, e.g., hash oil, tincture, or combination thereof.

As used herein, the term "inbreeding" refers to the production of offspring via the mating between relatives. The plants resulting from the inbreeding process are referred to herein as "inbred plants" or "inbreds".

As used herein, a "line" refers to a population of plants derived from a single cross, backcross or selfing. The individual offspring plants are not necessarily identical to one another. As distinguished from a "variety," a "line" displays less variation between individuals, generally (although not exclusively) by virtue of several generations of self-pollination. For purposes of this disclosure, a "line" is defined sufficiently broadly to include a group of plants vegetatively or clonally propagated from a single parent plant, using stem cuttings or tissue culture techniques. "Vegetative propagation", as used herein, refers to asexual propagation of the plant that is accomplished by taking and propagating cuttings, by grafting or budding, by layering, by division of plants, or by separation of specialized structure, such as stem, roots, tubers, rhizomes, or bulbs.

The term "breeding line", as used herein, refers to a line of a cultivated crop having commercially valuable or agronomically desirable characteristics, as opposed to wild varieties or landraces. The term includes reference to an elite breeding line or elite line, which represents a line of plants used to produce commercial F1 hybrids. An elite breeding line is obtained by breeding and selection for superior agronomic performance comprising a multitude of agronomically desirable traits.

The term "hybrid", as used herein, refers to any offspring of a cross between two genetically non-identical individuals. The parental plants may be related, as in production of a modified single cross, or unrelated. F1 hybrid, as used herein, refers to the first generation progeny of the cross of two genetically dissimilar plants.

The term "plant part" refers to any part of a plant including, but not limited to, organelles, single cells and cell tissues such as plant cells that are intact in plants, cell clumps and tissue cultures from which *cannabis* plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, and calli. The two main parts of plants grown in some sort of media, such as soil, are often referred to as the "above-ground" part, also often referred to as the "shoots", and the "below-ground" part, also often referred to as the "roots". The term "*cannabis* plant material" is to be interpreted as encompassing plant material derived from one or more *Cannabis* plants.

As used herein, "progeny" includes descendants of a particular plant or plant line. Progeny of an instant plant include seeds formed on F1, F2, F3, F4, F5, F6 and subsequent generation plants, or seeds formed on BC1, BC2, BC3, and subsequent generation plants, or seeds formed on F1BC1, FiBC2, FiBC3, and subsequent generation plants. The designation F1 refers to the progeny of a cross between two parents that are genetically distinct. The designations F2, F3, F4, F5 and F6 refer to subsequent generations of self- or sib-pollinated progeny of an F1 plant "Synergy" refers to the phenomenon where a first compound stimulates a first level of a particular activity, where a second compound stimulates a second level of the same particular activity, and where the presence of both compounds results in a third level of the same particular activity, where the third level is greater than the additive sum of the first level and the second level. Synergy can occur where the first compound and second compound are used at the same time, or where the first compound and second compound are used sequentially As used herein, "trichome" refers to a fine outgrowth or appendage on plants and certain protists. They are of diverse structure and function. In reference to *Cannabis*, the trichome is a glandular trichome that occurs most abundantly on the floral calyxes and bracts of female plants.

The term "variety" as used herein has the meaning to the corresponding definition in the International Convention for the Protection of New Varieties of Plants (UPOV Treaty). Thus, "variety" refers to a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Headings, e.g., (a), (b), (i) etc., are presented merely for ease of reading the specification and claims. The use of headings in the specification or claims does not require the steps or elements be performed in alphabetical or numerical order or the order in which they are presented.

Methods of the Disclosure

In one aspect, some embodiments disclosed herein relate to a method of making a composition for imparting one or more desired effects to a subject. The method includes preparing a composition in which a plurality of chemical compounds which are known to occur in a *cannabis* strain and are associated with at least one desired effect in a subject are enriched, wherein the amounts or levels of the plurality of chemical compounds with respect to one another in the composition are about the amounts or levels of the plurality of chemical compounds with respect to one another in the *cannabis* strain.

In principle, the methods according to the present disclosure can be applied to any plant, strain, varieties, and/or lines. Particularly suitable species include members of the plant family Cannabaceae. In some embodiments, the plant species is a species belonging to the genera *Cannabis* and *Humulus*. Non-limiting examples of *Humulus* species suitable for the compositions and methods disclosed herein include *Humulus japonicus* (syn. *H. scandens*), *Humulus lupulus*, *Humulus lupulus* var. *lupulus*, *Humulus lupulus* var. *cordifolius*, *Humulus lupulus* var. *lupuloides* (syn. *H. americanus*), *Humulus lupulus* var. *neomexicanus*, and *Humulus lupulus* var. *pubescens*. In some embodiments, the plant species is a species belonging to the genus *Cannabis*.

*Cannabis* is a genus of flowering plant that includes three species (and seven taxa) or subspecies, *C. sativa*, *C. indica*, and *C. ruderalis*. The plant is an annual, dioecious, flowering herb indigenous to central Asia and the Indian subcontinent. *Cannabis* is commonly reproduced by self-pollination and fertilization. This type of sexual reproduction facilitates the preservation of plant and variety characteristics during breeding and seed production. The preservation of these characteristics is often important to plant breeders for producing *Cannabis* plants having desired traits. *Cannabis* normally has imperfect flowers, with staminate "male" and pistillate "female" flowers occurring on separate plants. It is not unusual, however, for individual plants to bear both male and female flowers. Although monoecious plants are often referred to as "hermaphrodites", true hermaphrodites (which are less common) bear staminate and pistillate structures together on individual flowers, whereas monoecious plants bear male and female flowers at different locations on the same plant. Male flowers are normally borne on loose panicles, and female flowers are borne on racemes.

*Cannabis* is diploid, having a chromosome complement of 2n=20, although polyploid individuals have been artificially produced. The first genome sequence of *Cannabis*, which is estimated to be 820 Mb in size, was published in 2011 by Bakel et al., (Genome Biology 12(10): R102, 2011). All known strains of *Cannabis* are wind-pollinated and the fruit is an achene. Most strains of *Cannabis* are short day plants, with the possible exception of *C. sativa* subsp. *sativa* var. *spontanea* (=*C. ruderalis*), which is commonly described as "auto-flowering" and may be day-neutral.

The *Cannabis* plant material has been reported to contain suitable and desirable compounds, useful in various pharmaceutical dosage forms and methods of medical treatment. The suitable and desirable compounds may include, for example, one or more the following classes of compounds: cannabinoids, terpenoids, and flavonoids. These compounds can be obtained from the *Cannabis* in a pure or enriched state. The compounds obtained from the *Cannabis* can be in the form of an extract of *Cannabis*, or a concentrate of *Cannabis*.

For example, *Cannabis* has long been used for hemp fiber, for hemp oils, for medicinal purposes, and as a recreational drug. Industrial hemp products are made from *cannabis* plants selected to produce an abundance of fiber. The *Cannabis* plant can produce a wide variety of chemicals and compounds. About 140 of these belong to a large class of aromatic organic hydrocarbons known as terpenes and terpenoids. The main difference between terpenes and terpenoids is that terpenes are hydrocarbons; whereas, terpenoids have been denatured by oxidation (which may occur during drying and curing the flowers) or chemically modified.

Terpenes are synthesized in *cannabis* in secretory cells inside glandular trichomes, and production is increased with light exposure. These terpenes are mostly found in high concentrations in unfertilized female *cannabis* flowers prior to senescence (the condition or process of deterioration with age). The essential oil is extracted from the plant material by steam distillation or vaporization. Many terpenes vaporize around the same temperature as the cannabinoid $\Delta(9)$-tetrahydrocannabinol (THC) which boils at about 157° C., but some terpenes are more volatile than others. Terpenes also play an important role by providing the plant with natural protection from bacteria and fungus, insects and other environmental stresses.

Terpenes have been found to be essential building blocks of complex plant hormones and molecules, pigments, sterols and even cannabinoids. Most notably, terpenes are responsible for the pleasant or not so pleasant, aromas of *cannabis* and the physiological effects associated with them. Patients will often ask to smell the *cannabis* when selecting their medicine. The idea is that certain aromas help identify different strains and their effects.

It has been reported that medical marijuana strains can vary greatly from one source to another, and even from one harvest to another. Those with relatively high concentrations of specific terpenes do, however, make them easier to identify by their smell than other strains. Most agree that varieties that smell of musk or of clove deliver sedative, relaxing effects (high level of the terpene myrcene); piney smells help promote mental alertness and memory retention (high level of the terpene pinene); and lemony aromas are favored for general uplift in mood and attitude (high level of limonene).

*Cannabis* plants can exhibit wide variation in the quantity and type of cannabinoids they produce. The mixture of cannabinoids produced by a plant is known as the plant's cannabinoid profile. Selective breeding has been used to control the genetics of plants and modify the cannabinoid profile. For example, strains that are used as fiber (commonly called hemp) are bred such that they are low in psychoactive chemicals like THC. Strains used in medicine are often bred for high CBD content, and strains used for recreational purposes are usually bred for high THC content or for a specific chemical balance. Some *cannabis* strains have been bred to produce minimal levels of tetrahydrocannabinol (THC), the principal psychoactive constituent. Many *cannabis* plants have been selectively bred to produce a maximum of cannabinoids (such as THC and/or CDB), which can be obtained by curing the flowers. Various compounds, including hashish and hash oil, can be extracted from the *cannabis* plant.

Accordingly, in some embodiments, the methods disclosed herein include a biological sample from a *Cannabis* plant. Generally, the biological sample can be any sample derived from a *cannabis* plant, and can be, for example, a nucleic acid sample, a protein sample, or a plant part. The term "plant part" refers to any part of a plant including, but not limited to, organelles, single cells and cell tissues such as plant cells that are intact in plants, cell clumps and tissue cultures from which *cannabis* plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, and calli. The two main parts of plants grown in some sort of media, such as soil, are often referred to as the "above-ground" part, also often referred to as the "shoots", and the "below-ground" part, also often referred to as the "roots". In some embodiments, the *cannabis* plant part can include flower tissues and/or trichomes.

Suitable *cannabis* species include *Cannabis sativa, Cannabis indica,* or *Cannabis ruderalis*. Hybrid *cannabis* strains and inbred *cannabis* strains are both suitable. Non-limiting examples of preferred *cannabis* strains include, but not limited to ACDC PX, AG1 Lemon, AG2 Orange, Agent Orange, Blackberry Kush, Blue Dream, Bluebbery OG, Bubba Kush, Cherry Pie, Durban Poison, Fire OG, Girl Scout Cookies, Gorilla Glue, Grape Ape, Green Crack, Headband, Jack Herer, Jet Fuel, Kalashnikova, Keep Tahoe OG, Kosher Kush, Master Kush, OG Kush, Pineapple Express, Pineapple Xpress, Purple Haze, Purple Kush, Purple Trainwreck, SFV OG, Skywalker OG, Sour AK, Sour Diesel, Strawberry AK, Super Lemon Haze, Super Silver Haze, Tahoe OG, Terpin Gorilla, Trainwreck, Watermelon OG, White Widow. Additional examples of preferred *cannabis* strains include, but are not limited to, *cannabis* strains that have been deposited under NCIMB Nos. 41541, 42254, 42255, 42256, 42257, and 42258.

Accordingly, in some embodiments, the methods according to the present disclosure include a *cannabis* strain selected from the group consisting of ACDC PX, AG1 Lemon, AG2 Orange, Bluebbery OG, Jet Fuel, Kalashnikova, Keep Tahoe OG, Pineapple Xpress, Sour AK, Strawberry AK, Terpin Gorilla, and Watermelon OG. In some preferred embodiments, the *cannabis* strain is AG1 Lemon strain or AG2 Orange strain. In some embodiments, a representative seed sample of the *cannabis* strain has been deposited under NCIMB Nos. 41541, 42254, 42255, 42256, 42257, and 42258.

Implementations of embodiments of the method according to this aspect and other aspects of the present disclosure can include one or more of the following features. In some embodiments, the preparation of the composition includes (i) obtaining a first enriched or purified composition of a first chemical compound from among the plurality of chemical compounds associated with at least one desired effect in a subject and which is known to occur in a *cannabis* strain, and (ii) combining the first enriched or purified composition with a second enriched or purified composition of a second chemical compound from among the plurality of chemical compounds associated with at least one desired effect in a subject and which is known to occur in the *cannabis* strain. In some embodiments, the plurality of chemical compounds include one or more compounds selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements.

Terpenes

In some embodiments of methods and compositions disclosed herein, the plurality of enriched chemical compounds can include one or more terpene compounds. Terpenes are a large and diverse class of organic compounds, produced by a variety of plants. They are often strong smelling and thus may have had a protective function. Terpenes are derived biosynthetically from units of isoprene, which has the molecular formula C5H8. The basic molecular formulae of terpenes are multiples of that, $(C_5H_8)n$ where n is the number of linked isoprene units. The isoprene units may be linked together "head to tail" to form linear chains or they may be arranged to form rings. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids. Typically known for their olfactory stimulation, they are commonly used in the manufacture of chewing gum, candies and mints. They are also recognized for their diverse biological activity, often being touted as components which synergize with other endogenous and exogenous ligands. They are also recognized as entourage compounds, meaning that they increase the effects of ligands that bind to some receptors, while the terpenes themselves, have little affinity for the receptor.

In *cannabis* plants, terpenes naturally are biosynthesized from units of isoprene, which can be linked to form linear chains or rings. In increasing length, the terpenes include hemiterpenes (single isoprenoid unit), monoterpenes (two units), sesquiterpenes (three units), diterpenes (four units), sesterterpenes (five units), triterpenes (six units), and so on. Terpenes are also known as terpenoids.

The fragrance of fruits and flowers is primarily due to aerosolized terpenes that are registered by the olfactory receptor neurons in the nose. In citrus fruits, the major aromatic compounds are limonene (LIM) and eucalyptol (EUC), which are both terpenes. The aromatic compounds of clove oil include eugenol and β-caryophyllene (BCP), which are terpenes. The aromatic compounds of peppermint include LIM, menthone, and menthol, which are all terpenes.

The terpene composition of a sample, such as a plant, flower, fruit, leaves, etc. can be analyzed with analytical tools, such as chromatography or mass spectrometry. Nonetheless, establishing the actual type and amount of terpene in a sample can be difficult because there may be hundreds of different terpenes in a sample, and terpenes with very different properties may differ by only the stereochemistry at a single carbon atom. See, for example, the well-known difference between R-(−)-carvone, which smells like spearmint, and S-(+)-cavone, which smells like caraway. Accordingly, determining the type and amount of each terpene in a sample will often require the use of complimentary analytical techniques, such as LC-MS and GC-MS.

Some examples of terpenes, and their classification, are as follows.

Hemiterpenes: Examples of hemiterpenes, which do not necessarily have an odor, are 2-methyl-1,3-butadiene, hemialboside, and hymenoside.

Monoterpenes: pinene, α-pinene, β-pinene, cis-pinane, trans-pinane, cis-pinanol, trans-pinanol (Erman and Kane (2008) Chem. Biodivers. 5:910-919), limonene; linalool; myrcene; eucalyptol; α-phellandrene; β-phellandrene; α-ocimene; β-ocimene, cis-ocimene, ocimene, Δ-3-carene; fenchol; sabinene, borneol, isoborneol, camphene, camphor, phellandrene, α-phellandrene, α-terpinene, geraniol, linalool, nerol, menthol, myrcene, terpinolene, α-terpinolene, β-terpinolene, γ-terpinolene, Δ-terpinolene, α-terpineol, and trans-2-pinanol.

Sesquiterpenes: caryophyllene, caryophyllene oxide, humulene, α-humulene, α-bisabolene; β-bisabolene; santalol; selinene; nerolidol, bisabolol; α-cedrene, β-cedrene, β-eudesmol, eudesm-7(11)-en-4-ol, selina-3,7(11)-diene, guaiol, valencene, α-guaiene, β-guaiene, Δ-guaiene, guaiene, farnesene, α-farnesene, 0-farnesene, elemene, α-elemene, β-elemene, γ-elemene, Δ-elemene, germacrene, germacrene A, germacrene B, germacrene C, germacrene D, and germacrene E.

Diterpenes: oridonin, phytol, and isophytol.

Triterpenes: ursolic acid, oleanolic acid.

1.5 ene": guaia-1(10),11-diene can be characterized as 1.5 ene. Guaia-1(10),11-diene is halfway between a monoterpene and diterpene, in terms of how many isoprenoid units are present. Monoterpene is $C_{10}H_{16}$, and diterpene is $C_{20}H_{32}$. Guaia-1(10),11-diene is $C_{15}H_{24}$. Isoprene is $C_5H_8$ (two double bonds).

Terpenoids, also known as isoprenoids, are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Plant terpenoids are used extensively for their aromatic qualities. They play a role in traditional herbal remedies and are under investigation for antibacterial, antineoplastic, and other pharmaceutical functions. The terpene Linalool for example, has been found to have anti-convulsant properties (Elisabetsky et al., Phytomedicine, May 6(2):107-13 1999). Well-known terpenoids include citral, menthol, camphor, salvinorin A in the plant *Salvia* divinorum, and the cannabinoids found in *Cannabis*. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

In some embodiments of the present disclosure, the plurality of enriched chemical compounds which are known to occur in a *cannabis* strain and are associated with at least one desired effect in a subject includes at least one *cannabis* terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds can include at least one, at least two, at least three, at least four, at least five, at least six, at least seven, at least eight, at least nine, at least ten, at least eleven, or at least twelve terpene compounds. In some embodiments, the plurality of chemical compounds can include 1, 2, 3, 4, 5, 6, 7, 8, 9, or 10 terpene compounds. In some embodiments, the plurality of chemical compounds includes at least one terpene compound selected from the group consisting of 3-carene, α-bisabolol, 0-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the plurality of chemical compounds includes at least one terpene compound selected from the group consisting of caryophyllene, limonene, linalool, myrcene, α-pinene, and β-pinene. In some embodiments, the plurality of chemical compounds includes at least one terpene compound selected from the group consisting of caryophyllene, myrcene, and α-pinene.

In accordance with the methods and compositions of the present disclosure, terpene compounds can be acquired commercially, in various purities, and are useful biochemical agents for a variety of olfactory and physiologically stimulating purposes. There are suppliers of terpenes that are pure and homogeneous, contract laboratories that synthesize terpenes, and contract laboratories that purify terpenes from natural products, e.g., essential oils, are available (see, e.g., Sigma-Aldrich, St. Louis, Mo.; TCI America, Portland, Oreg.; Arizona Chemical, Jacksonville, Fla.). Without implying any limitation, the term "pure" can refer to a terpene that is over 95% pure, over 98% pure, over 99% pure, over 99.5% pure, over 99.9% pure, over 99.99% pure, and the like. Generally, the term "pure" does not take into account any solvent that may be used for dissolving the terpene, such as a solvent that is ethanol, acetone, tetrahydrofuran, and so on. In other words, unless specified otherwise, either explicitly or by the context, any solvent that is present is not relevant to the characterization of a given terpene as pure and homogeneous.

Generally, the one or more terpene compounds can be incorporated in the compositions and methods of the present disclosure in any suitable concentrations, which can be determined based on requirements of specific end applications. In this regard, a number of physiological parameters have been developed in the past decades and documented in various studies of mammalian, such as human, subject's response to administration of terpene compounds. These parameters include blood oxygen saturation, pulse rate, breathing rate, eye-blinks, skin conductance, skin temperature, and surface electromyogram (Heuberger et al., Neuropsychopharmacology. 29:1925-1932, 2004). Various subjective parameters can also be tested, in subject response to terpenes, including subjective attentiveness, mood, cheerfulness, subjective relaxation, vigor, calmness, and alertness (see, e.g., Heuberger et al (2004) Neuropsychopharmacology. 29:1925-1932; Diego et al. (1998) Int. J. Neurosci. 96:217-224; Knasko (1992) Chem. Senses. 17; 27-35), have a number of sensory tests can also be used for assessing subjective responses to variety of terpene-containing oils (Sugawara et al. J. Home Econ. Jpn. 49:1281-1290, 1998; Sugawara et al. Molecules. 18:3312-3338, 2013; Satoh and Sugawara, Analytical Sciences. 19:139-146, 2003). In these tests, the terpene-containing oils were tested for subjective impressions, that is, fresh-stale, soothing-activating, airy-heavy, plain-rich, natural-unnatural, elegant-unrefined, soft-strong, pleasant-unpleasant, warm-cool, comfortable-uncomfortable, woodsy-not woodsy, floral-peppery, lively-dull. Sugawara's group also provided methods for the statistical analysis of data on subjective response, for example, calculation of the p value and electroencephalography data.

In some embodiments, the amounts or levels of the plurality of terpene compounds relative to one another in the composition are about the amounts or levels of the plurality of terpene compounds relative to one another in a *cannabis* strain. In some preferred embodiments, the amounts or levels of the plurality of terpene compounds relative to one another in the composition are about the amounts or levels of the plurality of terpene compounds relative to one another in a *cannabis* strain as set forth in FIGS. 1-12.

In some embodiments, the total amount of terpenes in the prepared composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the total amount of terpenes in the composition is about 25%, about 50%, or about 75% of the total volume.

Isolation and Analysis of Terpenes

In accordance with the present disclosure, *cannabis* terpenes can be purified, analyzed, and identified, by any one of methodologies and techniques known in the art. Non-limiting examples of suitable methodologies and techniques include high pressure liquid chromography (HPLC), gas chromatography, and other chromatographic techniques (see, e.g., Musenga et al. J. Sep. Sci. 29:1251-1258, 2006; Yang et al. J. Nat. Prod. 72:484-487, 2009; Jella et al. J. Agric. Food Chem. 46:242-247, 1998; Andrea et al. J. Agric. Food Chem. 51:4978-4983, 2003; Villa et al. J. Pharm. Biomed. Anal. 44:755-762, 2007).

Other suitable techniques suitable for analysis and/or quantification of *cannabis* terpenes and other chemicals include, but are not limited to, mass spectrometry (Hendriks and Bruins, Biol. Mass Spectrom. 10:377-381, 1983); gas chromatography-mass spectrometry (GC-MS) (Gadulo et al. J. Food Sci. 75:C199-207, 2010), nuclear magnetic resonance (NMR) (Mucci et al., Food Chem. 141:3167-3176, 2013; Zhang et al., Food Chem. 138:208-213, 2013); mass spectroscopy; and Matrix-Assisted Laser Desorption/Ionization Time-of-Flight mass spectrometry (MALDI-TOF) (Scalarone et al., J. Mass Spectrom. 40:1527-1535, 2005).

Essential Oils

In some embodiments, the methods and compositions as disclosed herein can further include one or more specific essential oils. The essential oil suitable for the methods and compositions disclosed herein can generally be any essential oil and can include, but are not limited to, almond oil, anise oil, armoise oil, bergamote oil, cajeput oil, cardamom oil, cinnamon leaf oil, citronella oil, clove oil, cymbopogon oil (lemongrass), cypress oil, *eucalyptus* oil, fennel oil, geranium oil, girfole oil, grapefruit oil, jasmine oil, lavandin oil, lemon oil, lime oil, mandarin oil, mint oil, myrtle oil, neroli bigarade oil, *ocimum* oil, orange oil, patchouli oil, pepper oil, petitgrain oil, pine oil, rosemary oil, santalum oil, spearmint oil, thyme oil, valerian oil, *verbena* oil, vetiver oil, and wintergreen oil. In some particular embodiments, the methods and compositions disclosed herein include an amount of lime oil. In some embodiments, the methods and compositions as disclosed herein can exclude one or more of the essential oils above. In some particular embodiments, the methods and compositions disclosed herein specifically exclude lime oil. In some embodiments, the compositions and methods disclosed herein specifically exclude essential oil (i.e., no essential oil is present).

In principle, the one or more essential oil can be incorporated into the compositions and methods of the disclosure at any suitable concentrations. In some particular embodiments, the final concentration of essential oil in the compositions and methods disclosed herein is at least about 0.1%, at least about 0.2%, at least about 0.5%, at least about 1%, at least about 2%, at least about 3%, at least about 4%, at least about 5%, or at least about 10%, at least about 15%, or at least about 20% by volume. In various embodiments of the disclosure, the final concentration of essential oil in the composition is from about 0.1% to about 10%, from about 0.1% to about 15%, from about 0.5% to about 20%, about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the final concentration of essential oil in the compositions and methods disclosed herein is about 5%, 10%, or 15%. In some embodiments, the final concentration of essential oil in the compositions and methods disclosed herein is about 5%. In some embodiments, the final concentration of essential oil in the compositions and methods disclosed herein is about 15%.

Cannabinoids

In some embodiments of methods and compositions disclosed herein, the plurality of enriched chemical compounds can include one or more cannabinoid compounds. Cannabinoids are among the most studied group of secondary metabolites in *Cannabis*. Most exist in two forms, as acids and in neutral (decarboxylated) forms. The acid form is designated by an "A" at the end of its acronym (i.e. THCA). The cannabinoids are synthesized in the plant as acid forms, and while some decarboxylation does occur in the plant, it increases significantly post-harvest and the kinetics increase at high temperatures. The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

Phytocannabinoids, also called natural cannabinoids or herbal cannabinoids, are compounds produced by botanicals, most commonly *Cannabis sativa* L. and are often found in both carboxylated, acidic, and neutral forms, such as cannabidiolic acid (CBDA) and cannabidiol (CBD), respectively. Neutral phytocannabinoids can be derived from heating cannabinoid acids to perform the event referred to as decarboxylation. At least 85 different cannabinoids have been isolated from the *Cannabis* plants (El-Alfy et al., 2010, *Pharmacology Biochemistry and Behavior* 95 (4): 434-42). Various cultivars of *Cannabis sativa* L. can produce varying cannabinoid ratios and unique and diverse cannabinoid profiles, with their cannabinoids being produced in the trichomes of the plant, often in a sticky icky resinous form comprised with associated terpenes. These components are cytotoxic to the plant and are thus produced and stored in the trichomes to ward of predators and used in chemical botanical warfare.

In some embodiments, the plurality of enriched chemical compounds can include at least one, at least two, at least three, at least four, at least five, at least six, at least seven, at least eight, at least nine, at least ten, at least eleven, or at least twelve cannabinoid compounds. In some embodiments, the plurality of enriched chemical compounds can include 1, 2, 3, 4, 5, 6, 7, 8, 9, or 10 cannabinoid compounds. In some embodiments of the disclosure, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA). In some embodiments, the methods and compositions as disclosed herein can exclude one or more of the cannabinoid compounds described above. In some particular embodiments, the methods and compositions disclosed herein specifically exclude THC and/or CBD. In some embodiments, the compositions and methods disclosed herein specifically exclude cannabinoids (i.e., no cannabinoid is present).

Generally, the one or more cannabinoid compounds can be incorporated in the compositions and methods of the present disclosure in any suitable concentrations, which can be determined based on requirements of specific end applications. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In various embodiments of the disclosure, the amount of the one or more cannabinoid compound is from about 1% to about 50%, from about 10% to about 80%, from about 20% to about 90%, from about 30% to about 98% from about 5% to about 15%, from about 10% to about 25%, from about 20% to about 35%, from about 30% to about 45%, from about 40% to about 55%, or from about 80% to about 98% of the total volume.

Medium-Chain Triglyceride—MCT

In some embodiments, the methods and compositions disclosed herein can include one or more medium-chain fatty acid triester of glycerol, which is also known as medium-chain triglyceride—MCT. Medium-chain triglycerides (MCTs) are triglycerides whose fatty acids have an aliphatic tail of 6-12 carbon atoms. The fatty acids found in MCTs are called medium-chain fatty acids (MCFAs). Like all triglycerides, MCTs are composed of a glycerol backbone and three fatty acids. In the case of MCTs, 2 or 3 of the fatty acid chains attached to glycerol are of medium length. Non-limiting examples of MCFAs include caproic acid (C6:0), caprylic acid (C8:0), capric acid (C10:0), and lauric acid (C12:0). In addition, apart from the above listed straight chain (unbranched chain) fatty acids, side chain (branched chain) fatty acids, e.g. nonanoic acid, are other examples of medium-chain fatty acids. MCTs are bland compared to other fats and do not generate off-notes (dissonant tastes) as quickly as long-chain triglycerides (LCTs). They are also more polar than LCTs. The addition of MCT was used initially as a dilutant. However, recent research indicates that the MCT creates a more bioavailable composition. In addition, due to their ability to be absorbed rapidly by the body, medium-chain triglycerides have found use in the treatment of a variety of malabsorption ailments. Because of these attributes, they are widely used as solvents for flavors and oral medicines and vitamins.

Accordingly, in some embodiments of the disclosure, the MCT of the compositions and methods disclosed herein includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the methods and compositions as disclosed herein can exclude one or more of the MCTs described above. In some embodiments, the compositions and methods disclosed herein specifically exclude MCTs (i.e., no MCT is present). In some embodiments, when the methods and compositions as disclosed herein include one or more MCTs, at least one of the one or more MCTs is an MCT derived from *cannabis* seed.

In some embodiments, the ratio of the MCT amount to the amount of the at least one terpene compound is from about 1:1000 to about 1000:1 by volume. In various embodiments of the disclosure, the ratio of the MCT amount to the amount of the at least one terpene compound is from about 1:1000 to about 100:1, from about 1:1000 to about 10:1, from about 100:1 to about 10:1, from about 1:500 to about 500:1, from about 1:100 to about 100:1, from about 1:20 to about 20:1, from about 10:1 to about 1:10, from about 1:50 to about 5:1, from about 1:2 to about 2:1. In some embodiments, the ratio of the MCT amount to the amount of the at least one terpene compound is about 100:1 to about 3:1 by volume. In some embodiments, the ratio of the MCT amount to the amount of the at least one terpene compound is about 50:1, about 40:1, about 30:1, about 20:1, about 10:1, about 5:1, about 3:1, about 2:1, or about 1:1. In some embodiments, the ratio of the MCT amount to the amount of the at least one terpene compound is about 3:1.

In one aspect, some embodiments disclosed herein relate to a method for characterizing a *cannabis* strain, which includes identifying one or more genetic characteristics present in a biological sample from the *cannabis* strain wherein the one or more genetic characteristics are associated with a desired level or amount of one or more chemical compounds in the *cannabis* strain which is associated with at least one desired effect in a subject.

In some embodiments, the method includes determining a plurality of genetic or epigenetic characteristics in a biological sample from the *cannabis* strain. The number of genetic or epigenetic characteristics can generally be any numbers. For example, in some embodiments, the plurality of genetic or epigenetic characteristics includes at least 2, at least 5, at least 10, at least 15, at least 20, at least 25, at least 50, or at least 100 genetic or epigenetic characteristics. In general, the plurality of genetic or epigenetic characteristics can be selected from any types of genetic or epigenetic characteristics or a combination of any thereof. For example, in some embodiments, the plurality of genetic or epigenetic characteristics in the biological sample can include at least one molecular genetic marker selected from the group consisting of a simple sequence repeat (SSR), a cleaved amplified polymorphic sequence (CAPS), a simple sequence length polymorphism (SSLP), a restriction fragment length polymorphism (RFLP), a random amplified polymorphic DNA (RAPD) marker, a single nucleotide polymorphism (SNP), an amplified fragment length polymorphism (AFLP), an insertion, a deletion, an InDel mutation, an epigenetic alteration, a splicing variant, and a haplotype created from two or more of the above described molecular genetic marker. In some embodiments, the plurality of genetic or epigenetic characteristics in the biological sample can include at least one molecular genetic marker in conjunction with one or more phenotypic measurements, microarray data, analytical measurements (e.g., an RNA/protein overexpression, and an aberrant RNA/protein expression), biochemical measurements, environmental measurements, or transcription levels.

In accordance with the present disclosure, genetic or epigenetic characteristics in the biological sample can be identified by one or more methodologies or techniques known in the art. Non-limiting examples of methodologies or techniques suitable for the identification of one or more genetic or epigenetic characteristics in the biological sample as disclosed herein includes performing an analytical assay selected from the group consisting of nucleic acid sequencing, polypeptide sequencing, restriction digestion, nucleic acid amplification-based assays, nucleic acid hybridization assay, capillary electrophoresis, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), in-silico comparative genomics, methylation analysis, linkage disequilibrium analysis, bioinformatics analysis, and an enzymatic activity assay. In some embodiments, the identification of the one or more genetic or epigenetic characteristics in the biological sample comprises an antibody-based assay selected form the group consisting of ELISA, immunohistochemistry, western blotting, mass spectrometry, flow cytometry, protein-microarray, immunofluorescence, and a multiplex detection assay. In some embodiments, the one or more genetic or epigenetic characteristics is selected from the genetic markers described by Bakel et al. (Genome Biology 12(10): R102, 2011), the content of which is hereby incorporated by reference in its entirety. In some embodiments, the one or more genetic or epigenetic characteristics in the biological sample is selected from the PE2EUKC3372906, PE2EUKC3373261, PE2EUKC3373508, PE2EUKC3373607, PE2EUKC3375323, PE2EUKC3376354, PE2EUKC3378841, PE2EUKC3379537, PE2EUKC3383039 alleles of the cannabinoid synthase gene. In some embodiments, the one or more genetic or epigenetic characteristics in the biological sample is selected from the PE2EUKC3373123, PE2EUKC3373262, PE2EUKC3373344, PE2EUKC3373785, PE2EUKC3373853, PE2EUKC3373917, PE2EUKC3374045, PE2EUKC3374046, PE2EUKC3374480, PE2EUKC3374792, PE2EUKC3374920, PE2EUKC3374958, PE2EUKC3376119, PE2EUKC3376254, PE2EUKC3376800, PE2EUKC3376880, PE2EUKC3376881, PE2EUKC3377036, PE2EUKC3377775, PE2EUKC3377954, PE2EUKC3378831, PE2EUKC3379063, PE2EUKC3379603, PE2EUKC3385636, PE2EUKC3398153 alleles of the terpene synthase genes. In some embodiments, the one or more genetic or epigenetic characteristics includes at least 2, at least 3, at least 4, at least 5, at least 6, at least 10, at least 20, at least 50, or at least 100 genetic or epigenetic characteristics. In some embodiments, the method according to this aspect and other aspects of the present disclosure includes determining a plurality of genetic or epigenetic characteristics associated with a desired level or amount of a plurality of chemical compounds in the *cannabis* strain. In some embodiments, the plurality of chemical compounds in the *cannabis* strain is selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements. In some embodiments, the plurality of chemical compounds in the *cannabis* strain includes at least one terpene compounds. In some embodiments, the plurality of chemical compounds in the *cannabis* strain includes at least one cannabinoid compounds. In some embodiments, the plurality of chemical compounds includes at least 2, at least 3, at least 4, at least 5, at least 10, at least 15, at least 20, at least 25, at least 30, at least 35, or at least 40 chemical compounds.

In a related aspect, the present disclosure also provides a method of determining a profile of the amounts or levels of a plurality of chemical compounds associated with at least one desired effect in a subject, the method includes (i) obtaining a *cannabis* plant sample including the plurality chemical compounds, and (ii) determining the amounts or levels of the plurality chemical compounds in the *cannabis* plant sample.

Accordingly, in some embodiments, the present disclosure relates to the enrichment or isolation and analysis of naturally-occurring chemical compounds from a *cannabis* plant, and also the preparation of enriched chemical compositions that mimic those compositions found in nature.

In some embodiments, the method according to this aspect includes: generating a library of chemical profiles, obtaining a biological sample, analyzing a chemical profile of the sample to identify a plurality of chemical compounds in the sample; quantifying the chemical compounds identified; and generating a database of chemical profiles based on those quantities. In some embodiments, the method further includes preparing an enriched chemical composition or a blend of chemical compounds that mimics one or more of the compositions and/or profiles represented in the database.

The sample can be from any plant or other natural product, including species of the genera *Cannabis* and *Humulus*. The analysis step may comprise separating chemical compounds from a mixture, genetic analysis, chemotaxonomic analysis, compound extraction, gas chromatography flame ionization detection, chemical formula identification, chromatography, or any other analytical chemistry technique described herein or otherwise known in the art. Chemical compounds such as, terpenes can be identified based on their chromatography profiles or other chemical properties of the analyzed compounds. Terpenes identified can be those listed in FIGS. 1-12, or any other terpenes. Terpenes may be quantified based on their mass fraction, percent weight, mole fraction, percentage by volume, or the like. The compounds and their quantities can be assembled as a library or database, or any other data management format known in the art. In embodiments that involve creating a prepared blend that mimics a naturally-occurring composition, the synthetic blend may comprise one or more naturally-occurring chemical compounds described herein, all of those chemical compounds, or a combination thereof.

In some embodiments, the present disclosure provides a composition that is further formulated into a liquid form. Non-limiting examples of suitable liquid formulation include a transparent liquid, a translucent liquid, an opaque liquid, a slurry, an emulsion, a suspension, a gel, and the like. The designation of liquid, slurry, emulsion, gel, and so on, refers to this characterization as determined at room temperature (e.g., about 23 degrees centigrade).

In some embodiments, one or more of various additional components can be included in the compositions as disclosed herein in order to achieve the desired properties. Suitable components include, but are not limited to, dipropylene glycol, phytol, isophytol, diethyl phthalate, isoparaffins, paraffins, silicon oils, perfluorinated aliphatic ethers, polyethylene glycols, glycol ethers, glycol ether esters, esters, ketones, propylene glycol, ethanol, dimethicone, and cyclomethicone.

In some embodiments, one or more solvents can be included. For example, solvents such as propylene glycol are commonly used in electronic cigarette (e-cigarette) formulations. For example, the addition of 10-70% cannabinoids to a mixture of terpenes and propylene glycol creates an emulsified mixture suitable for use in e-cigarettes.

In accordance with the present disclosure, the chemical profile of a biological sample, such as a plant, flower, fruit, leaves, etc. can be analyzed with one or more analytical assays and techniques such as, for example, chromatography or mass spectrometry. Nonetheless, establishing the actual type and amount of terpene in a sample can be difficult because there may be hundreds of different terpenes in a sample, and terpenes with very different properties may differ by only the stereochemistry at a single carbon atom. See, for example, the well-known difference between R-(−)-carvone, which smells like spearmint, and S-(+)-cavone, which smells like caraway. Accordingly, determining the type and amount of each terpene in a sample will often require the use of complimentary analytical techniques, such as LC-MS and GC-M.

Quantitative analysis of a plant's cannabinoid profile is often determined by gas chromatography (GC), or more reliably by gas chromatography combined with mass spectrometry (GC/MS). Liquid chromatography (LC) techniques are also possible and, unlike GC methods, can differentiate between the acid and neutral forms of the cannabinoids.

Accordingly, in some embodiments of the methods disclosed herein, the determination of the level or amount of the plurality of chemical compounds includes an analytical assay selected from gas chromatography (GC), flame ionization detector (FID), thin layer chromatography (TLC) analysis, and high performance liquid chromatography (HPLC). In certain embodiments, the analytical assay used to determine the level or amount of the plurality of chemical compounds includes a GC-FID or GC-MS with headspace analyzer. In certain embodiments, the analytical assay used to determine the level or amount of the plurality of chemical compounds includes in injection analysis with GC-FID or HPLC.

In principle, the methods according to the present disclosure can be applied to any *cannabis* plant, strain, varieties, and/or lines. Particularly suitable species include members of the genera *Cannabis* and *Humulus*. In some embodiments, the plant species is a species belonging to the genus *Cannabis*.

Suitable *cannabis* species include *Cannabis sativa, Cannabis indica,* or *Cannabis ruderalis*. Hybrid *cannabis* strains and inbred *cannabis* strains are both suitable. Non-limiting examples of preferred *cannabis* strains include, but not limited to ACDC PX, AG1 Lemon, AG2 Orange, Agent Orange, Blackberry Kush, Blue Dream, Bluebbery OG, Bubba Kush, Cherry Pie, Durban Poison, Fire OG, Girl Scout Cookies, Gorilla Glue, Grape Ape, Green Crack, Headband, Jack Herer, Jet Fuel, Kalashnikova, Keep Tahoe OG, Kosher Kush, Master Kush, OG Kush, Pineapple Express, Pineapple Xpress, Purple Haze, Purple Kush, Purple Trainwreck, SFV OG, Skywalker OG, Sour AK, Sour Diesel, Strawberry AK, Super Lemon Haze, Super Silver Haze, Tahoe OG, Terpin Gorilla, Trainwreck, Watermelon OG, White Widow. Additional examples of preferred *cannabis* strains include, but are not limited to, *cannabis* strains that have been deposited under NCIMB Nos. 41541, 42254, 42255, 42256, 42257, and 42258.

Accordingly, in some embodiments, the compositions and methods according to the present disclosure include a *cannabis* strain selected from the group consisting of ACDC PX, AG1 Lemon, AG2 Orange, Bluebbery OG, Jet Fuel, Kalashnikova, Keep Tahoe OG, Pineapple Xpress, Sour AK, Strawberry AK, Terpin Gorilla, and Watermelon OG. In some preferred embodiments, the *cannabis* strain is AG1 Lemon strain or AG2 Orange strain. In some embodiments, a representative seed sample of the *cannabis* strain has been deposited under NCIMB Nos. 41541, 42254, 42255, 42256, 42257, and 42258.

Compositions of the Disclosure

In one aspect, some embodiments disclosed herein relate to a composition for imparting one or more desired effects to a subject, wherein a plurality of chemical compounds which are known to occur in a *cannabis* strain and are associated with at least one desired effect in a subject are enriched in the composition and wherein the amounts or levels of the plurality of chemical compounds with respect to one another in the composition are about the amounts or levels of the plurality of chemical compounds with respect to one another in the *cannabis* strain. As described in further detail below, implementations of embodiments of the composition according to this aspect and other aspects of the disclosure can include one or more of the following features.

In some embodiments, the composition includes (i) a first enriched or purified composition of a first chemical compound from among the plurality of chemical compounds associated with at least one desired effect in a subject and which is known to occur in a *cannabis* strain, and (ii) a second enriched or purified composition of a second chemical compound from among the plurality of chemical compounds associated with at least one desired effect in a subject and which is known to occur in the *cannabis* strain.

In some embodiments, the plurality of chemical compounds includes at least one terpene compound selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements.

In some embodiments, the plurality of chemical compounds which are known to occur in a *cannabis* strain and are associated with at least one desired effect in a subject includes at least one *cannabis* terpene compound selected from the group consisting of monoterpenes, diterpenes, triterpenes, hemiterpenes, sesquiterpenes, sesterterpenes, sesquarterpenes, and notisoprenoids. In some embodiments, the plurality of chemical compounds can include at least one, at least two, at least three, at least four, at least five, at least six, at least seven, at least eight, at least nine, at least ten, at least eleven, or at least twelve terpene compounds. In some embodiments, the plurality of chemical compounds includes 1, 2, 3, 4, 5, 6, 7, 8, 9, or 10 terpene compounds. In some embodiments, the plurality of chemical compounds includes at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, In some embodiments, the plurality of chemical compounds includes at least one terpene compound selected from the group consisting of caryophyllene, limonene, linalool, myrcene, α-pinene, and β-pinene. In some embodiments, the plurality of chemical compounds includes at least one terpene compound selected from the group consisting of caryophyllene, myrcene, and α-pinene.

Generally, the one or more terpene compounds can be incorporated in the compositions of the present disclosure in any suitable concentrations, which can be determined based on requirements of specific end applications. In some embodiments, the amounts or levels of the plurality of terpene compounds relative to one another in the composition are about the amounts or levels of the plurality of terpene compounds relative to one another in a *cannabis* strain. In some preferred embodiments, the amounts or levels of the plurality of terpene compounds relative to one another in the composition are about the amounts or levels of the plurality of terpene compounds relative to one another in a *cannabis* strain as set forth in FIGS. 1-12. In some embodiments, the total amount of terpenes in the prepared composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the total amount of terpenes in the composition is about 25%, about 50%, or about 75% of the total volume.

In some embodiments, the compositions as disclosed herein can further include one or more specific essential oils. The essential oil suitable for the compositions disclosed herein can generally be any essential oil and can include, but are not limited to, almond oil, anise oil, armoise oil, bergamote oil, cajeput oil, cardamom oil, cinnamon leaf oil, citronella oil, clove oil, cymbopogon oil (lemongrass), cypress oil, *eucalyptus* oil, fennel oil, geranium oil, girfole oil, grapefruit oil, jasmine oil, lavandin oil, lemon oil, lime oil, mandarin oil, mint oil, myrtle oil, neroli bigarade oil, *ocimum* oil, orange oil, patchouli oil, pepper oil, petitgrain oil, pine oil, rosemary oil, santalum oil, spearmint oil, thyme oil, valerian oil, *verbena* oil, vetiver oil, and wintergreen oil. In some particular embodiments, the compositions disclosed herein include an amount of lime oil. In some embodiments, the compositions as disclosed herein can exclude one or more of the essential oils above. In some particular embodiments, the compositions disclosed herein specifically exclude lime oil. In some embodiments, the compositions disclosed herein specifically exclude essential oil (i.e., no essential oil is present).

In principle, the one or more essential oil can be incorporated into the compositions of the disclosure at any suitable concentrations. In some particular embodiments, the final concentration of essential oil in the compositions disclosed herein is at least about 0.1%, at least about 0.2%, at least about 0.5%, at least about 1%, at least about 2%, at least about 3%, at least about 4%, at least about 5%, or at least about 10%, at least about 15%, or at least about 20% by volume. In various embodiments of the disclosure, the final concentration of essential oil in the composition is from about 0.1% to about 10%, from about 0.1% to about 15%, from about 0.5% to about 20%, about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the final concentration of essential oil in the compositions disclosed herein is 5%, 10%, or 15%. In some embodiments, the final concentration of essential oil in the compositions disclosed herein is 5%. In some embodiments, the final concentration of essential oil in the compositions disclosed herein is 15%.

In some embodiments disclosed herein, the composition further includes one or more cannabinoid compound. In some embodiments, the one or more cannabinoid compound includes at least one phytocannabinoid. In some embodiments, the composition can include at least one, at least two, at least three, at least four, at least five, at least six, at least seven, at least eight, at least nine, at least ten, at least eleven, or at least twelve cannabinoid compounds. In some embodiments, the comp can include 1, 2, 3, 4, 5, 6, 7, 8, 9, or 10 cannabinoid compounds. In some embodiments of the disclosure, the one or more cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA). In some embodiments, the compositions as disclosed herein can exclude one or more of the cannabinoid compounds described above. In some particular embodiments, the compositions disclosed herein specifically exclude THC and/or CBD. In some embodiments, the compositions disclosed herein specifically exclude cannabinoids (i.e., no cannabinoid is present).

Generally, the one or more cannabinoid compounds can be incorporated in the compositions of the present disclosure in any suitable concentrations, which can be determined based on requirements of specific end applications. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In various embodiments of the disclosure, the amount of the one or more cannabinoid compound is from about 1% to about 50%, from about 10% to about 80%, from about 20% to about 90%, from about 30% to about 98% from about 5% to about 15%, from about 10% to about 25%, from about 20% to about 35%, from about 30% to about 45%, from about 40% to about 55%, or from about 80% to about 98% of the total volume.

In some embodiments, the composition can further include a medium-chain fatty acid triester of glycerol (medium-chain triglyceride—MCT). In some embodiments, the MCT of the compositions disclosed herein includes at least one medium-chain fatty acid having an aliphatic tail of 6-12 carbon atoms. In some embodiments, the at least one medium-chain fatty acid of the MCT is selected from the group consisting of caproic acid (hexanoic acid), caprylic acid (ocanoic acid), capric acid (decanoic acid), and lauric acid (dodecanoic acid). In some embodiments, the at least one medium-chain fatty acid of the MCT includes caprylic acid. In some embodiments, the methods and compositions as disclosed herein can exclude one or more of the MCTs described above. In some embodiments, the compositions and methods disclosed herein specifically exclude MTCs (i.e., no MCT is present).

In some embodiments, the ratio of the MCT amount to the amount of the at least one terpene compound is from about 1:1000 to about 1000:1 by volume. In various embodiments of the disclosure, the ratio of the MCT amount to the amount of the at least one terpene compound is from about 1:1000 to about 100:1, from about 1:1000 to about 10:1, from about 100:1 to about 10:1, from about 1:500 to about 500:1, from about 1:100 to about 100:1, from about 1:20 to about 20:1, from about 10:1 to about 1:10, from about 1:50 to about 5:1, from about 1:2 to about 2:1. In some embodiments, the ratio of the MCT amount to the amount of the at least one terpene compound is about 100:1 to about 3:1 by volume. In some embodiments, the ratio of the MCT amount to the amount of the at least one terpene compound is about 50:1, about 40:1, about 30:1, about 20:1, about 10:1, about 5:1, about 3:1, about 2:1, or about 1:1. In some embodiments, the ratio of the MCT amount to the amount of the at least one terpene compound is about 3:1.

In one aspect, some embodiments of the present disclosure relate to a non-naturally occurring composition for conferring a desired effect to a subject, the composition including one or more *cannabis* terpene and a medium-chain triglyceride (MCT).

In some embodiments of this aspect, the one or more *cannabis* terpene can be selected from the group consisting of monoterpenes, diterpenes, triterpenes, hemiterpenes, sesquiterpenes, sesterterpenes, sesquarterpenes, and notisoprenoids. In some embodiments, the one or more terpene compound includes at least one, at least two, at least three, at least four, at least five, at least six, at least seven, at least eight, at least nine, at least ten, at least eleven, or at least twelve terpene compounds. In some embodiments, the one or more terpene compound includes 1, 2, 3, 4, 5, 6, 7, 8, 9, or 10 terpene compounds. In some embodiments, the one or more *cannabis* terpene is selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene.

In some embodiments, the non-naturally occurring composition of the present disclosure includes at least two *cannabis* terpenes selected from the group consisting of caryophyllene, myrcene, and α-pinene. In some embodiments, the non-naturally occurring composition further includes one or more additional *cannabis* terpene compounds selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpenolene, terpinene, terpineol, and valencene. In some embodiments, the one or more additional *cannabis* terpene compounds is selected from the group consisting of the one or more terpene compounds are selected from the group consisting of caryophyllene, myrcene, α-pinene, limonene, linalool, and β-pinene.

The one or more terpene compounds can be generally incorporated in the non-naturally occurring compositions of the present disclosure in any suitable concentrations, which can be determined based on requirements of specific end applications. In some embodiments, the total amount of terpenes in the prepared composition is greater than about 5%, greater than about 10%, greater than about 25%, greater than about 30%, greater than about 40%, greater than about 50%, greater than about 60%, greater than about 68%, greater than about 70%, greater than about 80%, or greater than about 90% by volume. In some embodiments, the total amount of terpenes in the composition is from about 0.1% to about 95%, about 1% to about 95%, about 1% to about 68%, about 25% to about 99%, about 25% to about 95%, about 25% to about 70%, about 40% to about 80%, about 40% to about 68%, about 50% to about 95%, about 50% to about 68%, about 60% to about 95%, about 60% to about 80%, about 68% to about 95%, or about 68% to about 90% by volume. In some embodiments, the total amount of terpenes in the composition is about 25%, about 50%, or about 75% of the total volume.

In some embodiments, the non-naturally occurring compositions as disclosed herein can further include one or more specific essential oils. The essential oil suitable for the non-naturally occurring compositions disclosed herein can generally be any essential oil and can include, but are not limited to, almond oil, anise oil, armoise oil, bergamote oil, cajeput oil, cardamom oil, cinnamon leaf oil, citronella oil, clove oil, cymbopogon oil (lemongrass), cypress oil, *eucalyptus* oil, fennel oil, geranium oil, girfole oil, grapefruit oil, jasmine oil, lavandin oil, lemon oil, lime oil, mandarin oil, mint oil, myrtle oil, neroli bigarade oil, *ocimum* oil, orange oil, patchouli oil, pepper oil, petitgrain oil, pine oil, rosemary oil, santalum oil, spearmint oil, thyme oil, valerian oil, *verbena* oil, vetiver oil, and wintergreen oil. In some particular embodiments, the non-naturally occurring compositions disclosed herein include an amount of lime oil. In some embodiments, the non-naturally occurring compositions as disclosed herein can exclude one or more of the essential oils above. In some particular embodiments, the non-naturally occurring compositions disclosed herein specifically exclude lime oil. In some embodiments, the non-naturally occurring compositions disclosed herein specifically exclude essential oil (i.e., no essential oil is present).

In some embodiments, the final concentration of essential oil in the non-naturally occurring compositions disclosed herein is at least about 0.1%, at least about 0.2%, at least about 0.5%, at least about 1%, at least about 2%, at least about 3%, at least about 4%, at least about 5%, or at least about 10%, at least about 15%, or at least about 20% by volume. In various embodiments of the disclosure, the final concentration of essential oil in the composition is from about 0.1% to about 10%, from about 0.1% to about 15%, from about 0.5% to about 20%, about 0.1% to about 10%, from about 0.1% to about 5%, from about 0.5% to about 5%, from about 0.5% to about 5%, from about 0.5% to about 2%, from about 0.2% to about 5%, from about 0.2% to about 2%, from about 2% to about 5%, from about 2% to about 10%, from about 1% to about 3%, or from about 1% to about 5% by volume. In some embodiments, the final concentration of essential oil in the non-naturally occurring compositions disclosed herein is 5%, 10%, or 15%. In some embodiments, the final concentration of essential oil in the non-naturally occurring compositions disclosed herein is 5%. In some embodiments, the final concentration of essential oil in the non-naturally occurring compositions disclosed herein is 15%.

In some embodiments, the non-naturally occurring composition of the present disclosure further includes one or more cannabinoid compound. In some embodiments, the one or more cannabinoid compounds includes at least one phytocannabinoid. In some embodiments, the non-naturally occurring composition can include at least one, at least two, at least three, at least four, at least five, at least six, at least seven, at least eight, at least nine, at least ten, at least eleven, or at least twelve cannabinoid compounds. In some embodiments, the non-naturally occurring composition can include 1, 2, 3, 4, 5, 6, 7, 8, 9, or 10 cannabinoid compounds. In some embodiments, the at least one cannabinoid compound is selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), active analogues and derivatives of any one thereof. In some embodiments, the one or more cannabinoid compound is selected from the group consisting of Δ(9)-tetrahydrocannabinolic acid (THCA), Δ(9)-cannabidiolic acid (CBDA), active analogues and derivatives of any one thereof. In some embodiments, the one or more cannabinoid compound is selected from the group consisting of Δ(9)-tetrahydrocannabinolic acid (THCA), Δ(9)-tetrahydrocannabidiolic acid (CBDA). In some embodiments, the non-naturally occurring compositions as disclosed herein can exclude one or more of the cannabinoid compounds described above. In some particular embodiments, the non-naturally occurring compositions disclosed herein specifically exclude THC and/or CBD. In some embodiments, the non-naturally occurring compositions disclosed herein specifically exclude cannabinoids (i.e., no cannabinoid is present).

Generally, the one or more cannabinoid compounds can be incorporated in the non-naturally occurring compositions of the present disclosure in any suitable concentrations, which can be determined based on requirements of specific end applications. In some embodiments, the amount of the one or more cannabinoid compound is at least about 1%, at least about 2%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or at least about 98% of the total volume. In various embodiments of the disclosure, the amount of the one or more cannabinoid compound is from about 1% to about 50%, from about 10% to about 80%, from about 20% to about 90%, from about 30% to about 98% from about 5% to about 15%, from about 10% to about 25%, from about 20% to about 35%, from about 30% to about 45%, from about 40% to about 55%, or from about 80% to about 98% of the total volume.

In some embodiments, the medium-chain triglyceride (MCT) of the non-naturally occurring composition of the present disclosure includes at least one medium-chain fatty acid having an aliphatic tail of 6-12 carbon atoms. In some embodiments, the at least one medium-chain fatty acid is selected from the group consisting of caproic acid (hexanoic acid), caprylic acid (ocanoic acid), capric acid (decanoic acid), and lauric acid (dodecanoic acid). In some embodiments, the at least one medium-chain fatty acid comprises caprylic acid. In some embodiments, the ratio of the MCT amount to the amount of the at least one terpene compound is from about 1:1000 to about 1000:1 by volume. In various embodiments of the disclosure, the ratio of the MCT amount to the amount of the at least one terpene compound is from about 1:1000 to about 100:1, from about 1:1000 to about 10:1, from about 100:1 to about 10:1, from about 1:500 to about 500:1, from about 1:100 to about 100:1, from about 1:20 to about 20:1, from about 10:1 to about 1:10, from about 1:50 to about 5:1, from about 1:2 to about 2:1. In some embodiments, the ratio of the MCT amount to the amount of the at least one terpene compound is about 100:1 to about 3:1 by volume. In some embodiments, the ratio of the MCT amount to the amount of the at least one terpene compound is about 50:1, about 40:1, about 30:1, about 20:1, about 10:1, about 5:1, about 3:1, about 2:1, or about 1:1. In some embodiments, the ratio of the MCT amount to the amount of the at least one terpene compound is about 3:1.

In some embodiments, the desired effect in a subject can generally by any desired effect known to be associated with one or more of the chemical compounds which are known to occur in a *cannabis* strain. Non-limiting examples of the desired effect in a subject include, but are not limited to, reduced anxiety, reduced depression, improved alertness, cognitive ability enhancement, mood improvement, improved sleep quality, nausea reduction, pain relief, spasm relief, seizure decrease, muscle relaxation, antimicrobial, anti-diabetes, blood circulation improvement, psoriasis relief, anti-inflammation, relief of connective tissue disorder, bone stimulation, relief of rheumatoid arthritis, anti-oxidation, improvement to mobility (e.g., arthritis, multiple sclerosis), improvements to skin conditions (e.g., blemishes, scars, insect bites, hives, pimples), reduced seizures (epilepsy), reduction in hypertension, improved memory loss (e.g., dementia, Alzheimer's), reduced dependency on drugs (e.g. opioids, nicotine, alcohol), inhibition of cancer growth, increased metabolism, improvements to autoimmune disorders, appetite stimulation, reduced concussive injuries, and enhancement of skin penetration for transdermal delivery of therapeutic drug.

Without implying any limitation, other flavoring ingredients and/or modifiers can be included in the compositions and methods of the present disclosure. Non-limiting examples of such flavoring ingredients and/or modifiers include sweeteners, 4-hydroxy-2,5-dimethyl-3(2H)-furanone (strawberry), ethyl butyrate (apple, fruity), isoamyl acetate (banana), propyl hexanoate (pineapple, fruity), allyl hexanoate (pineapple, fruity), valencene (orange, fresh fruity), methyl anthranilate (also known as methyl 2-aminobenzoate) (grape), methyl butyrate (fruity, apple, pineapple), benzyl acetate (fruity, strawberry), p-mentha-8-thiol-3-one (grapefruit), (1S,4S)-trans-p-menthan-8-thiol-3-one acetate (black currant, exotic), (1R,4S)-cis-p-menthan-8-thiol-3-one acetate (fruity, sweet).

In some embodiments, the compositions of the present disclosure can be further formulated for administration orally, transdermally, topically, or parenterally. In some embodiments, the compositions of the present disclosure can be further formulated into a form selected from a tablet, a vaporizer inhalant, a capsule, a gel, a power, an oral spray, a chewable gum, a sublingual film or lozenge, and a transdermal patch. As used herein, "oral delivery" or "oral administration" refers to a route of administration wherein the pharmaceutical dosage form is taken through the mouth. Oral administration is a part of enteral administration, which also includes buccal (dissolved inside the cheek), sublabial (dissolved under the lip) and sublingual administration (dissolved under the tongue). Enteral medications come in various forms, including: tablets to swallow, chew or dissolve in water or under the tongue; capsules and chewable capsules (with a coating that dissolves in the stomach or bowel to release the medication there); time-release or sustained-release tablets and capsules (which release the medication gradually); powders or granules; teas; drops; and liquid medications or syrups. As used herein, "dermal delivery" or "dermal administration" refers to a route of administration wherein the pharmaceutical dosage form is taken to, or through, the dermis (i.e., layer of skin between the epidermis (with which it makes up the cutis) and subcutaneous tissues).

As used herein, "transdermal patch" or "adhesive topical patch" refers to a medicated adhesive patch that is placed on the skin to deliver a specific dose of medication through the skin and into the bloodstream. A transdermal patch or transdermal system (TDS) is a medicated adhesive patch that is placed on the skin to deliver a specific dose of drug through the skin and into the bloodstream. An advantage of a transdermal drug delivery route over other types of medication delivery such as oral, topical, intravenous, intramuscular, etc. is that the patch provides a controlled release of the medication into the patient, usually through either a porous membrane covering a reservoir of medication or through body heat melting thin layers of medication embedded in the adhesive. The main disadvantage to transdermal delivery systems stems from the fact that the skin is a very effective barrier; as a result, only medications whose molecules are small enough to penetrate the skin can effectively be delivered by this method.

The transdermal patch serves as an alternative dosage form for patients who experience dysphagia (difficulty in swallowing). Additional reasons to use transdermal patches include the convenience of a dosage form that can be taken without water as well as the inability of the patient to eat or drink (e.g., nausea and/or vomiting).

In some embodiments, the compositions of the present disclosure can be encapsulated for protection of aroma compounds for use in foods and other applications. As used herein, "capsule" refers to a solid pharmaceutical oral dosage form wherein the active (and inactive) ingredient is encapsulated. Encapsulation refers to a range of techniques used to enclose medicines in a relatively stable shell known as a capsule, allowing them to, for example, be taken orally or be used as suppositories. The two main types of capsules include hard-shelled capsules, which are typically made using gelatin and contain dry, powdered ingredients or miniature pellets made by, e.g. processes of extrusion or spheronisation. These are made in two halves: a lower-diameter "body" that is filled and then sealed using a higher-diameter "cape". The second main type of capsules include soft-shelled capsules, primarily used for oils and for active ingredients that are dissolved or suspended in oil. Both of these classes of capsules are made from aqueous solutions of gelling agents like such as animal protein mainly gelatin; and plant polysaccharides or their derivatives like carrageenans and modified forms of starch and cellulose. Other ingredients can be added to the gelling agent solution like plasticizers such as glycerin and/or sorbitol to decrease the capsule's hardness, coloring agents, preservatives, disintegrants, lubricants and surface treatment. In certain embodiments, the compositions of the present disclosure can be encapsulated with O-cyclodextrin. Methods, systems, and related materials useful for molecular encapsulation of flavor compounds derived from *Cannabis* are known in the art (Reineccius T A et al. Journal of Food Science, 68(4), 1234-1239, 2003; Yamamoto et al., Molecular encapsulation of citral or d-limonene flavor by spray drying; Rubiano et al., Ing. Compet. vol. 17 no. 2 Cali 2015). In certain embodiments, the compositions of the present disclosure are encapsulated in alginate beads as a protection and delivery system.

The discussion of the general methods and compositions given herein is intended for illustrative purposes only. Other alternative methods, compositions, and alternatives will be apparent to those of skill in the art upon review of this disclosure, and are to be included within the spirit and purview of this application.

EXAMPLES

Additional alternatives are disclosed in further detail in the following examples, which are not in any way intended to limit the scope of the claims.

Example 1

Generating Terpene Profiles of *Cannabis* Strains

In this Example, plant samples from 12 *cannabis* strains were analyzed for their chemical properties. The analytical process typically involved obtaining a *cannabis* plant sample, followed by analyzing a chemical profile of the plant samples to identify chemical compounds therein. In some analyses, the analytical process involved gas chromatography (GC) coupled with flame ionization detector (FID). In some other analyses, the analytical process involved high performance liquid chromatography (HPLC). The analysis step may further comprise other processes for extracting compounds or otherwise preparing the sample for analysis. Additionally, in some analyses, a gas chromatography-mass spectrometry (GCMS) was used to identify compounds using solid-phase micro-extraction (SPME). The analytical process also included quantifying chemical compounds by mass fraction, percent weight, mole fraction, percentage by volume. The determined quantities can be used to further determine ratios of chemical compounds to one another in the respective plant samples. Subsequently, those determined quantities, ratios, or other chemical properties were entered into a database of chemical profiles. In some experiments, the chemical profile database was used in conjunction with a genetic database with corresponding genetic or epigenetic characteristics identified in the plant samples.

Example 2

Chemical Profiling of *Cannabis* Strain AG1 Lemon

This Example describes the terpene profile of a sample derived from the *cannabis* strain "AG1 Lemon". Flower tissues were used. The analytical assay was GC/FID with Headspace Analyzer.

FIG. 1 provides an exemplary terpene profile of a plant sample derived from flower tissues of the *cannabis* strain "AG1 Lemon." The specific amounts of each of the terpene compounds present in the sample and the total terpene content are indicated.

Example 3

Chemical Profiling of *Cannabis* Strain AG2 Orange

This Example describes the terpene profile of a sample derived from the *cannabis* strain AG2 Orange. Flower tissues were used. The analytical assay was GC/FID with Headspace Analyzer.

Figure 2:
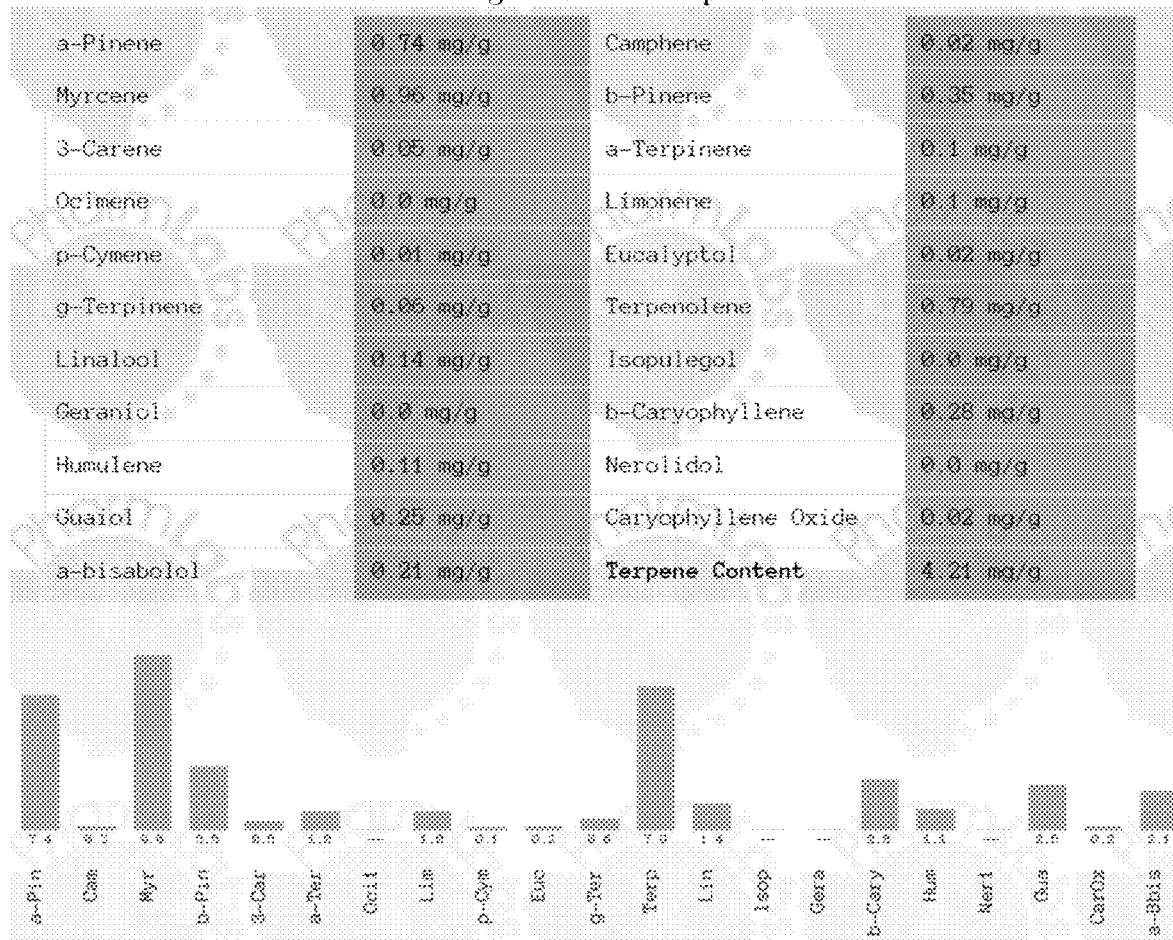
FIG. 2 shows an exemplary terpene profile of a plant sample derived from flower tissues of the *cannabis* strain "AG2 Orange." The specific amounts of each of the terpene compounds present in the sample and the total terpene content are indicated.

FIG. 2 provides an exemplary terpene profile of a plant sample derived from flower tissues of the *cannabis* strain "AG2 Orange." The specific amounts of each of the terpene compounds present in the sample and the total terpene content are indicated Example 4

Chemical Profiling of *Cannabis* Strain "Blueberry OG"

This Example describes the terpene profile of a sample derived from the *cannabis* strain "Blueberry OG". Flower tissues were used. The analytical assay was GC/FID with Headspace Analyzer.

Figure 3:
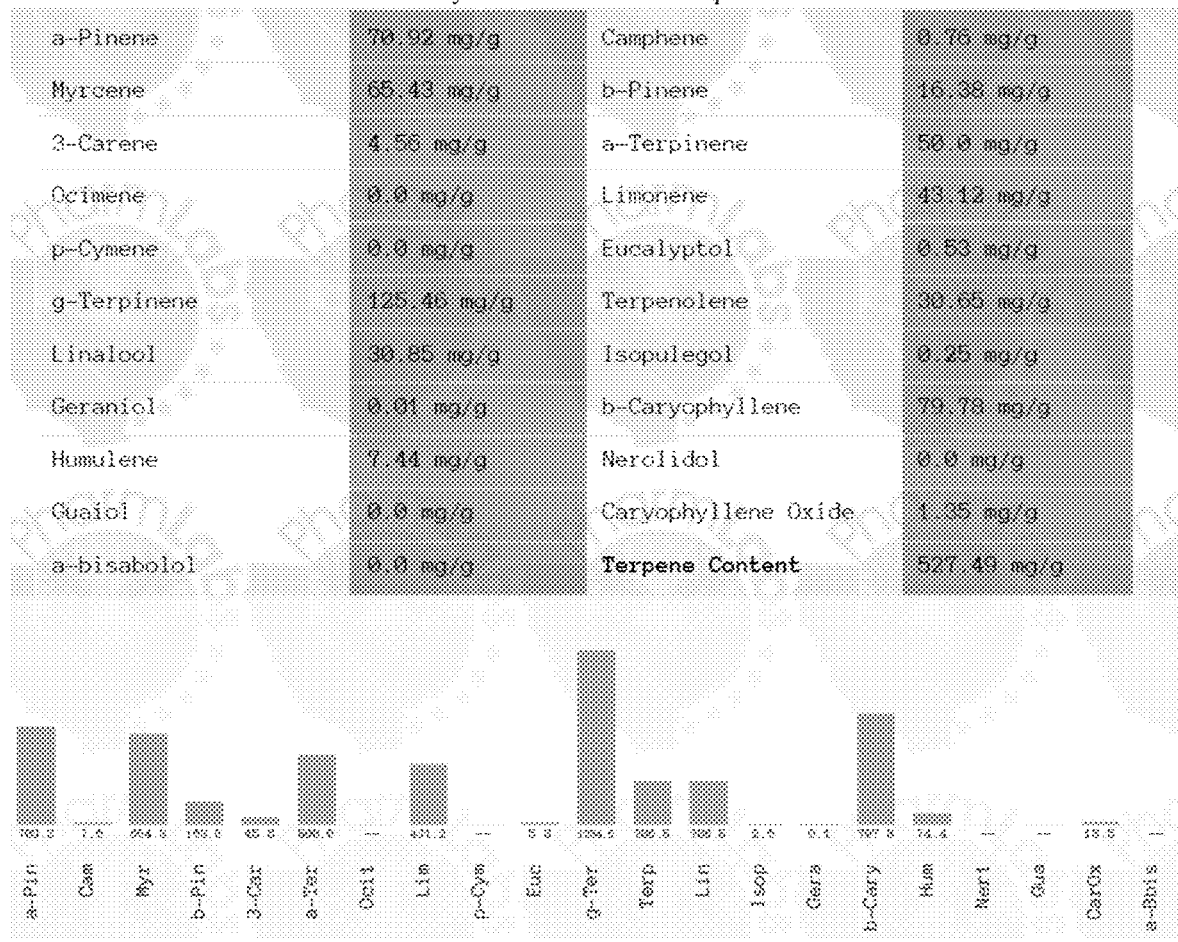
FIG. 3 illustrates an exemplary terpene profile of a plant sample derived from the *cannabis* strain "Blueberry OG." The specific amounts of each of the terpene compounds present in the sample and the total terpene content are indicated.

FIG. 3 provides an exemplary terpene profile of a plant sample derived from the *cannabis* strain "Blueberry OG." The specific amounts of each of the terpene compounds present in the sample and the total terpene content are indicated.

Example 5

Chemical Profiling of *Cannabis* Strain "Keep Tahoe OG"

This Example describes the terpene profile of a sample derived from the *cannabis* strain "Keep Tahoe OG". Flower tissues were used. The analytical assay was GC/FID with Headspace Analyzer.

Figure 4:
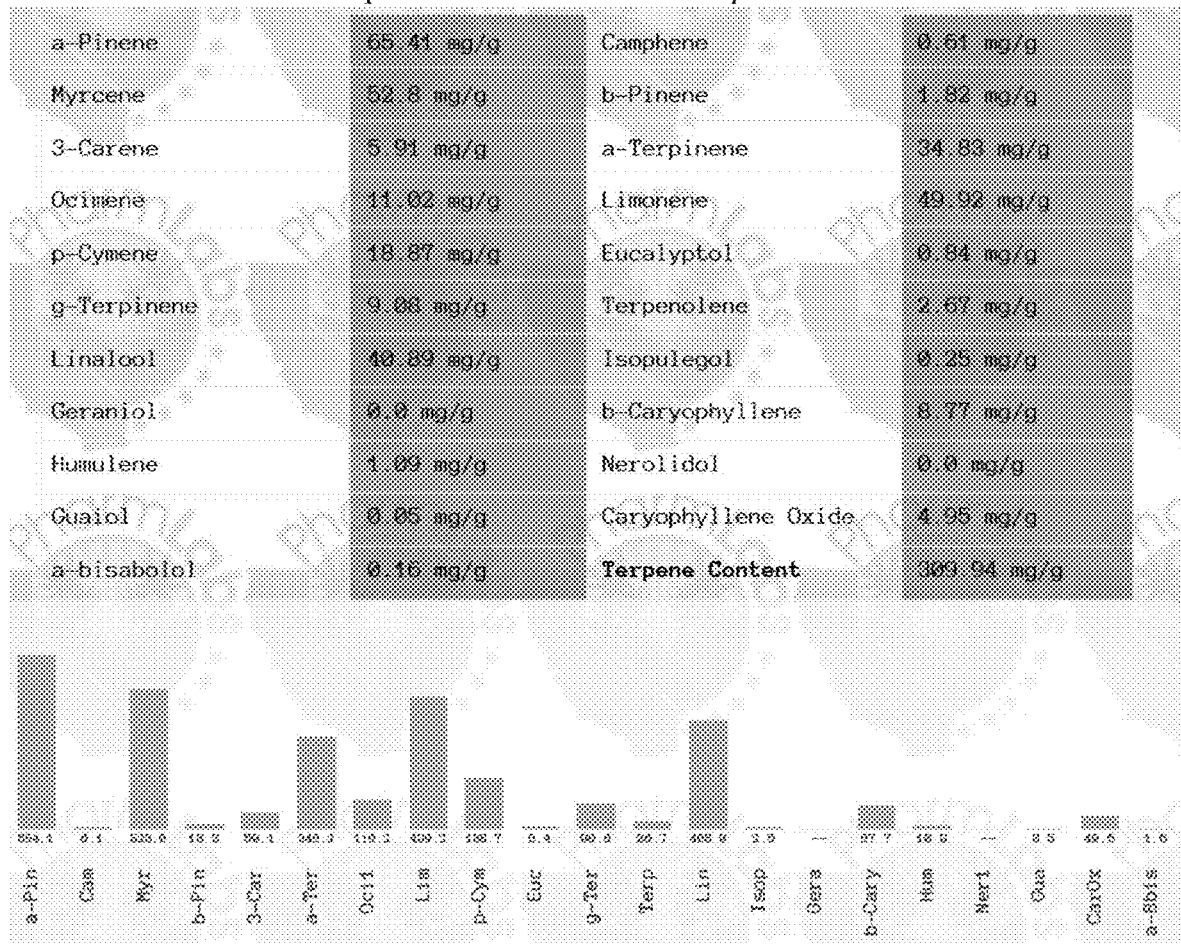
FIG. 4 shows an exemplary terpene profile of a plant sample derived from the *cannabis* strain "Keep Tahoe OG." The specific amounts of each of the terpene compounds present in the sample and the total terpene content are indicated.

FIG. 4 provides an exemplary terpene profile of a plant sample derived from the *cannabis* strain "Keep Tahoe OG." The specific amounts of each of the terpene compounds present in the sample and the total terpene content are indicated.

Example 6

Chemical Profiling of *Cannabis* Strain "ACDC PX"

This Example describes the terpene profile of a sample derived from the *cannabis* strain "ACDC PX". Flower tissues were used. The analytical assay was GC/FID with Headspace Analyzer.

Figure 5:
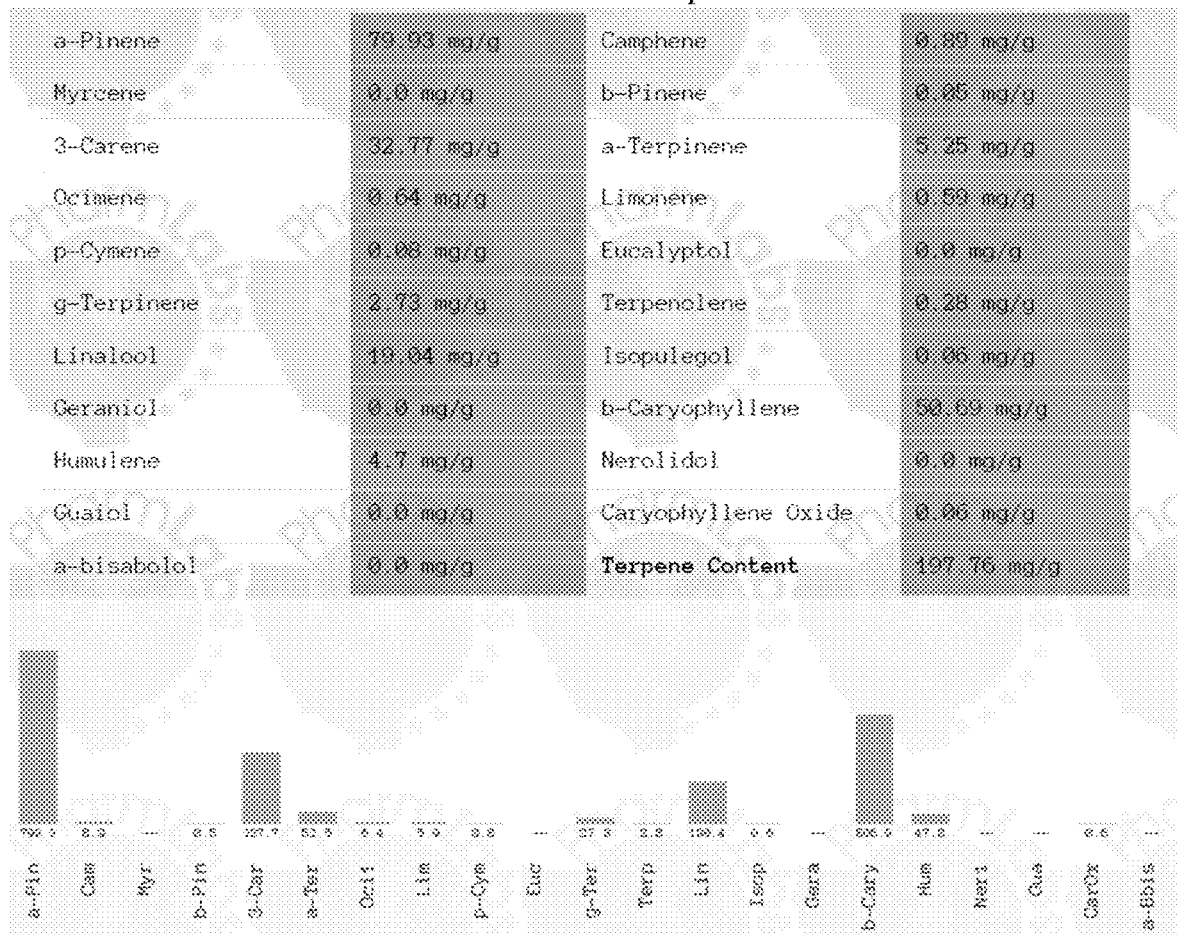
FIG. 5 is an exemplary terpene profile of a plant sample derived from the *cannabis* strain "ACDC PX." The specific amounts of each of the terpene compounds present in the sample and the total terpene content are indicated.

FIG. 5 provides a terpene profile of a plant sample derived from the *cannabis* strain "ACDC PX." The specific amounts of each of the terpene compounds present in the sample and the total terpene content are indicated.

Example 7

Chemical Profiling of *Cannabis* Strain "JetFuel"

This Example describes the terpene profile of a sample derived from the *cannabis* strain "JetFuel". Edible/tinctures (alcohol extracts of flower tissue) were used. The analytical assay was high performance liquid chromatography (HPLC).

Figure 6:
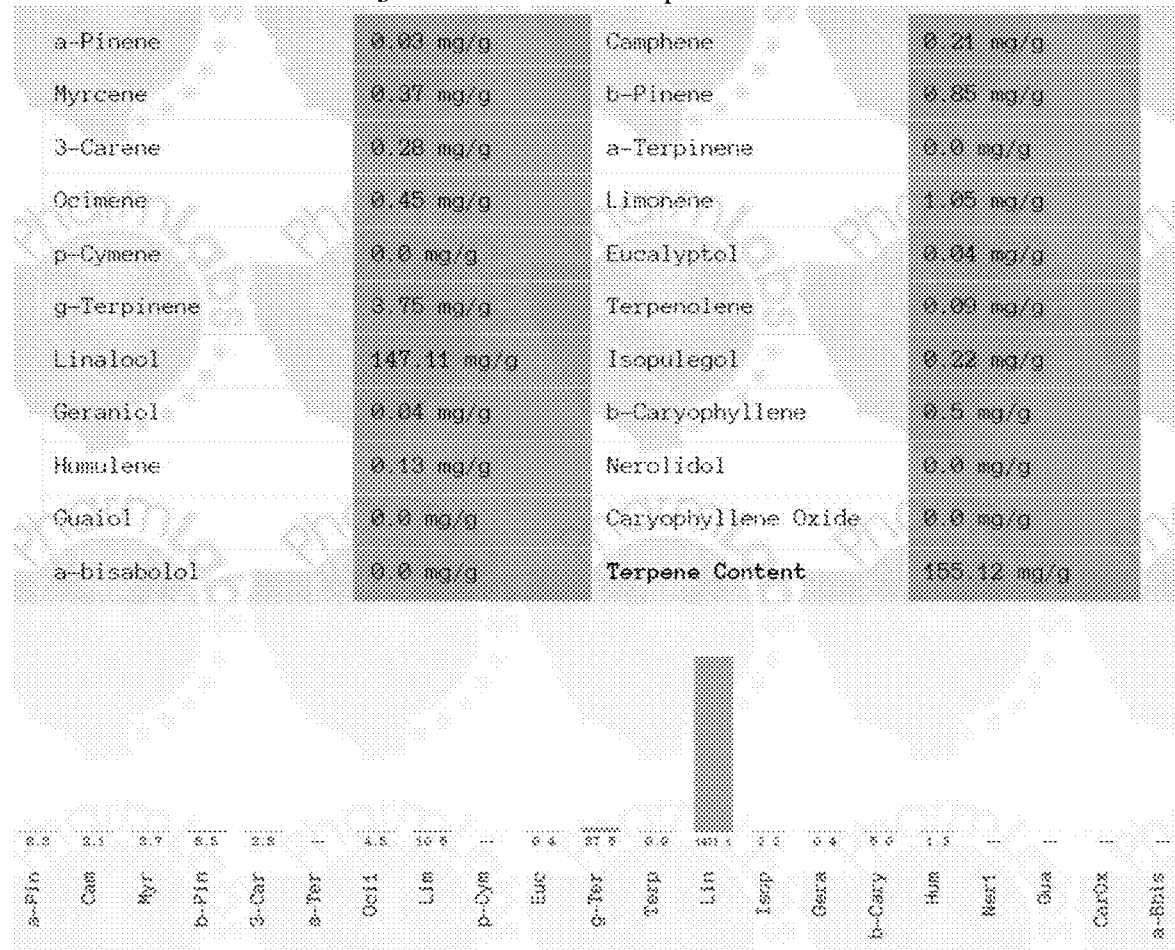
FIG. 6 shows an exemplary terpene profile of a plant sample derived from the *cannabis* strain "JetFuel." The specific amounts of each of the terpene compounds present in the sample and the total terpene content are indicated.

FIG. 6 provides an exemplary terpene profile of a plant sample derived from the *cannabis* strain "JetFuel." The specific amounts of each of the terpene compounds present in the sample and the total terpene content are indicated.

Example 8

Chemical Profiling of *Cannabis* Strain "Watermelon OG"

This Example describes the terpene profile of a sample derived from the *cannabis* strain "Watermelon OG". Edible/tinctures (alcohol extracts of flower tissue) were used. The analytical assay was high performance liquid chromatography (HPLC).

Figure 7:
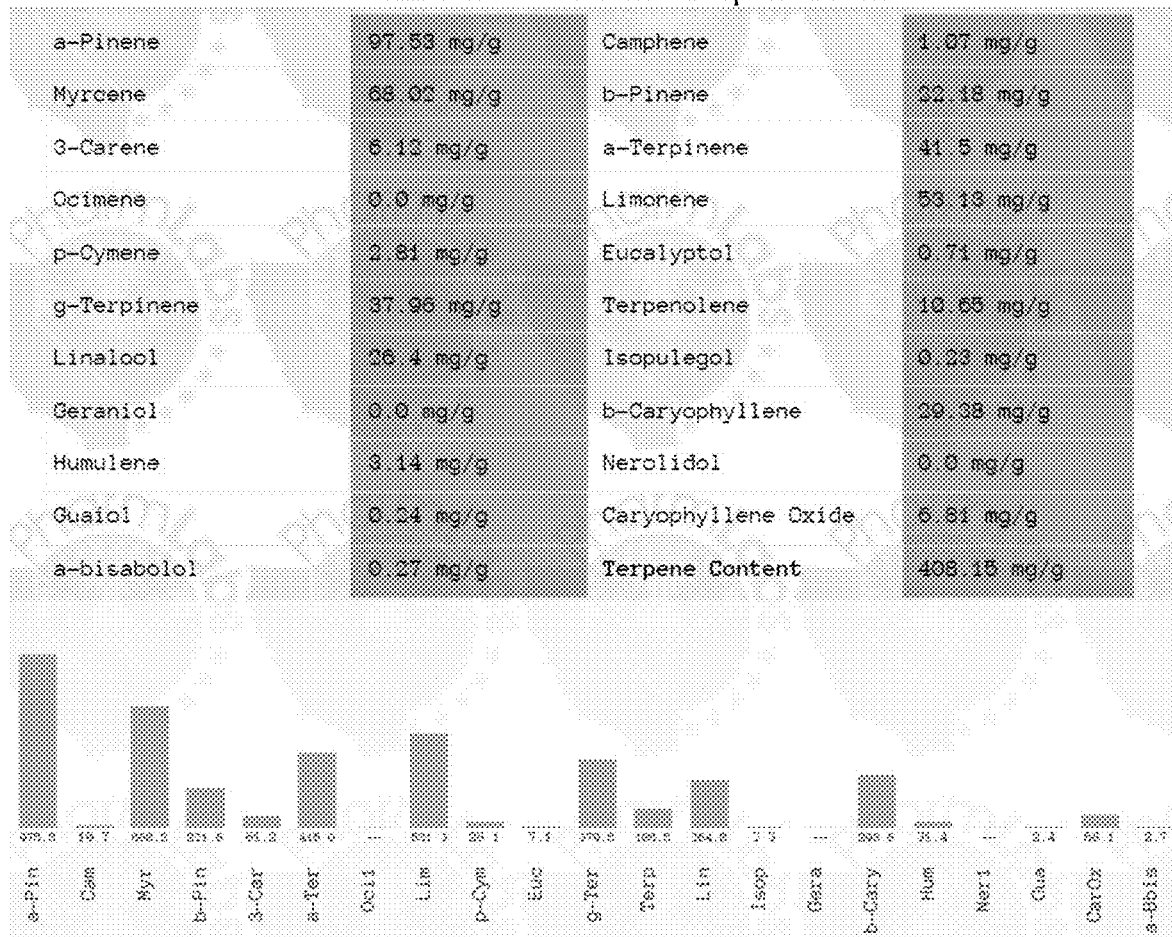
FIG. 7 illustrates an exemplary terpene profile of a plant sample derived from the *cannabis* strain "Watermelon OG." The specific amounts of each of the terpene compounds present in the sample and the total terpene content are indicated.

FIG. 7 provides an exemplary terpene profile of a plant sample derived from the *cannabis* strain "Watermelon OG." The specific amounts of each of the terpene compounds present in the sample and the total terpene content are indicated.

Example 9

Chemical Profiling of *Cannabis* Strain Terpin Gorilla

This Example describes the terpene profile of a sample derived from the *cannabis* strain "Terpin Gorilla". Flower tissues were used. The analytical assay was GC/FID with Headspace Analyzer.

Figure 8:
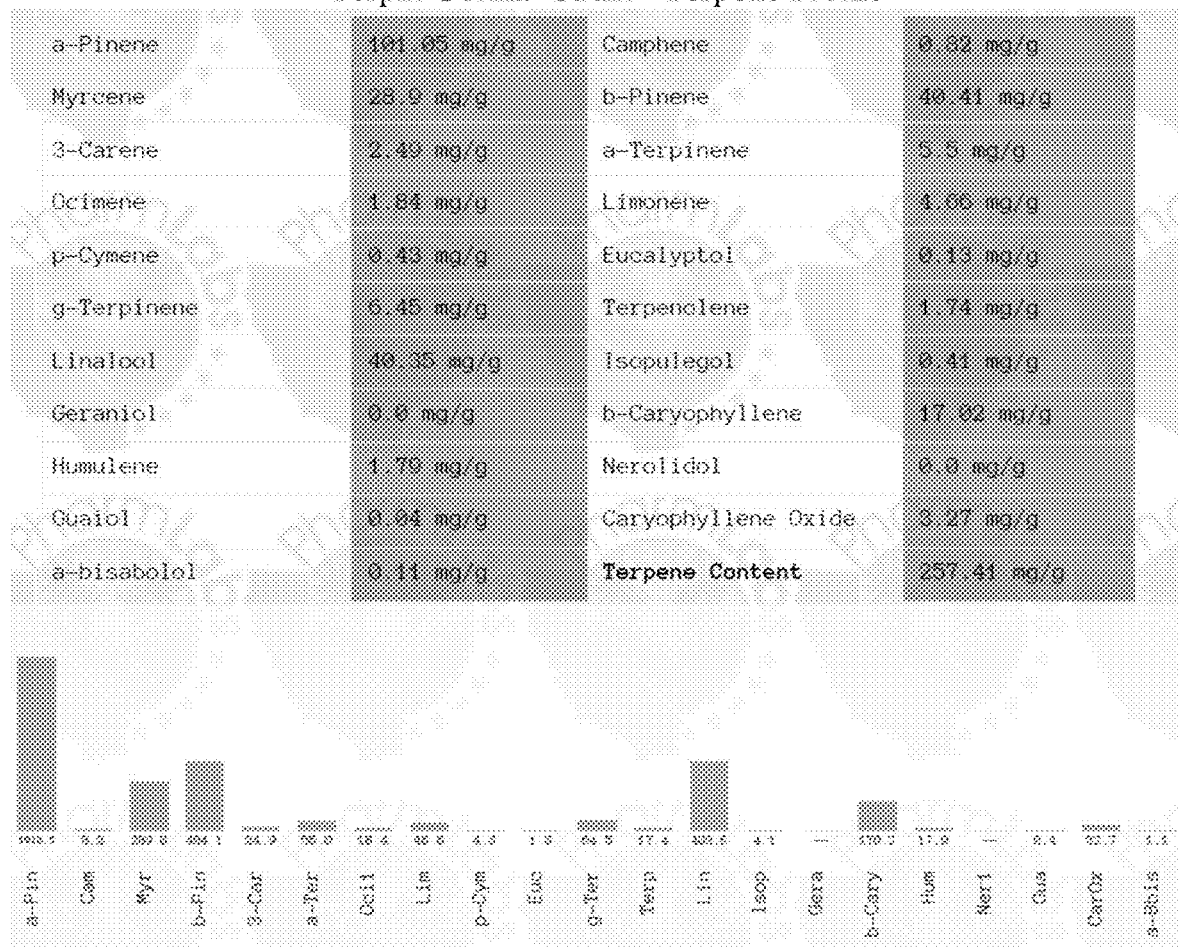
FIG. 8 is an exemplary terpene profile of a plant sample derived from the *cannabis* strain "Terpin Gorilla." The specific amounts of each of the terpene compounds present in the sample and the total terpene content are indicated.

FIG. 8 provides an exemplary terpene profile of a plant sample derived from the *cannabis* strain "Terpin Gorilla." The specific amounts of each of the terpene compounds present in the sample and the total terpene content are indicated.

Example 10

Chemical Profiling of *Cannabis* Strain "Strawberry AK"

This Example describes the terpene profile of a sample derived from the *cannabis* strain "Strawberry AK". Flower tissues were used. The analytical assay was GC/FID with Headspace Analyzer.

Figure 9:
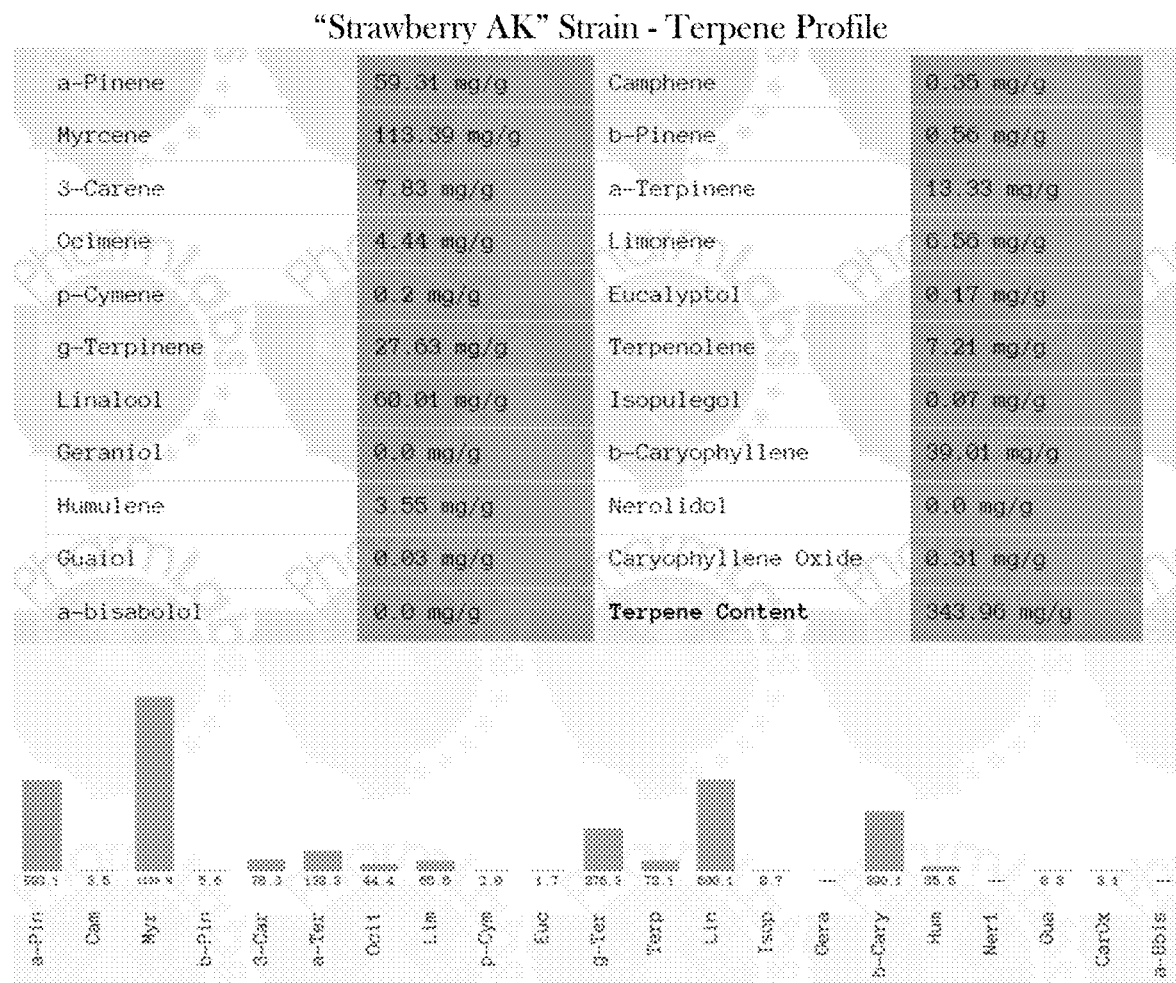
FIG. 9 is an exemplary terpene profile of a plant sample derived from the *cannabis* strain "Strawberry AK." The specific amounts of each of the terpene compounds present in the sample and the total terpene content are indicated.

FIG. 9 provides an exemplary terpene profile of a plant sample derived from the *cannabis* strain "Strawberry AK." The specific amounts of each of the terpene compounds present in the sample and the total terpene content are indicated.

Example 11

Chemical Profiling of *Cannabis* Strain "Sour AK"

This Example describes the terpene profile of a sample derived from the *cannabis* strain "Sour AK". Flower tissues were used. The analytical assay was GC/FID with Headspace Analyzer.

Figure 10:
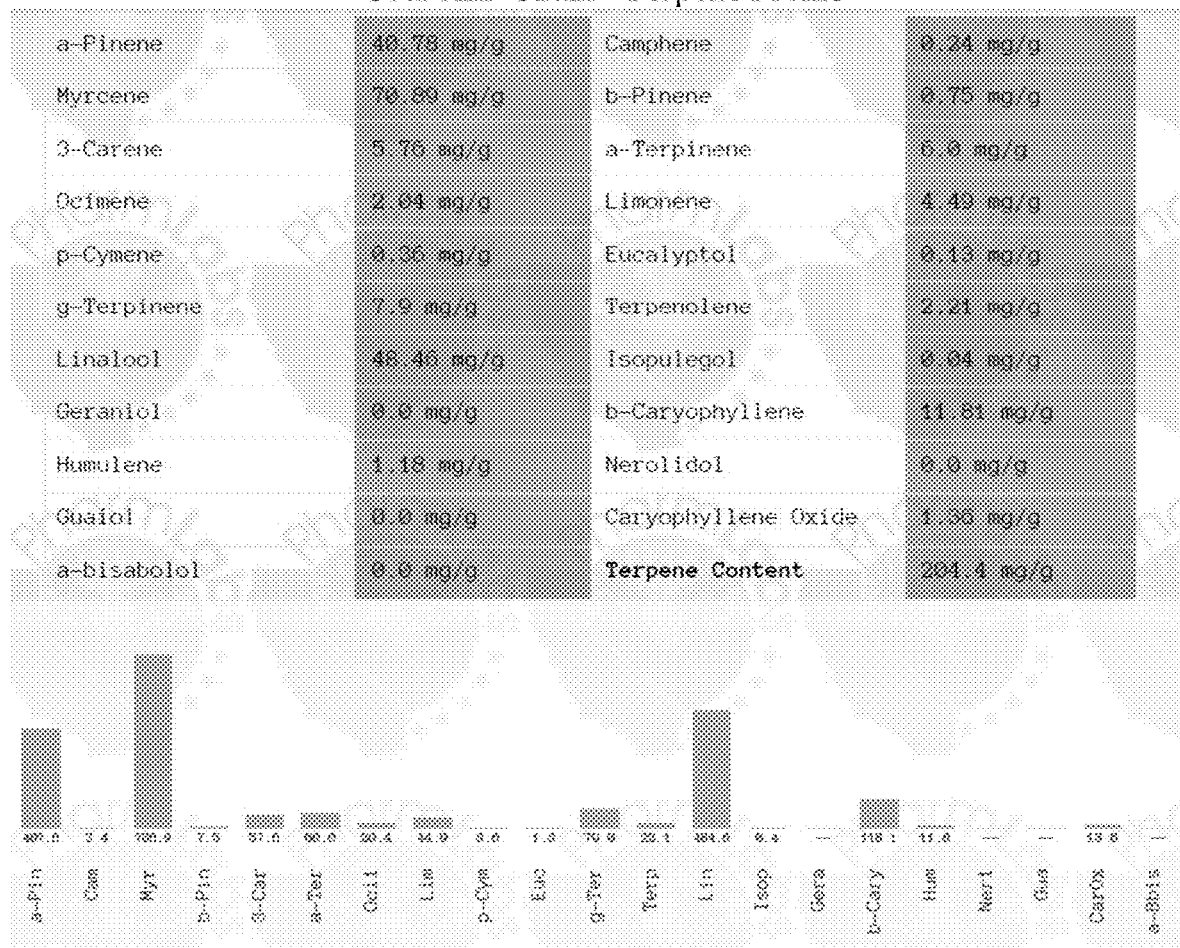
FIG. 10 shows an exemplary terpene profile of a plant sample derived from the *cannabis* strain "Sour AK." The specific amounts of each of the terpene compounds present in the sample and the total terpene content are indicated.

FIG. 10 provides an exemplary terpene profile of a plant sample derived from the *cannabis* strain "Sour AK." The specific amounts of each of the terpene compounds present in the sample and the total terpene content are indicated.

Example 12

Chemical Profiling of *Cannabis* Strain "Pineapple Xpress"

This Example describes the terpene profile of a sample derived from the *cannabis* strain "Pineapple Xpress". Flower tissues were used. The analytical assay was GC/FID with Headspace Analyzer.

Figure 11:
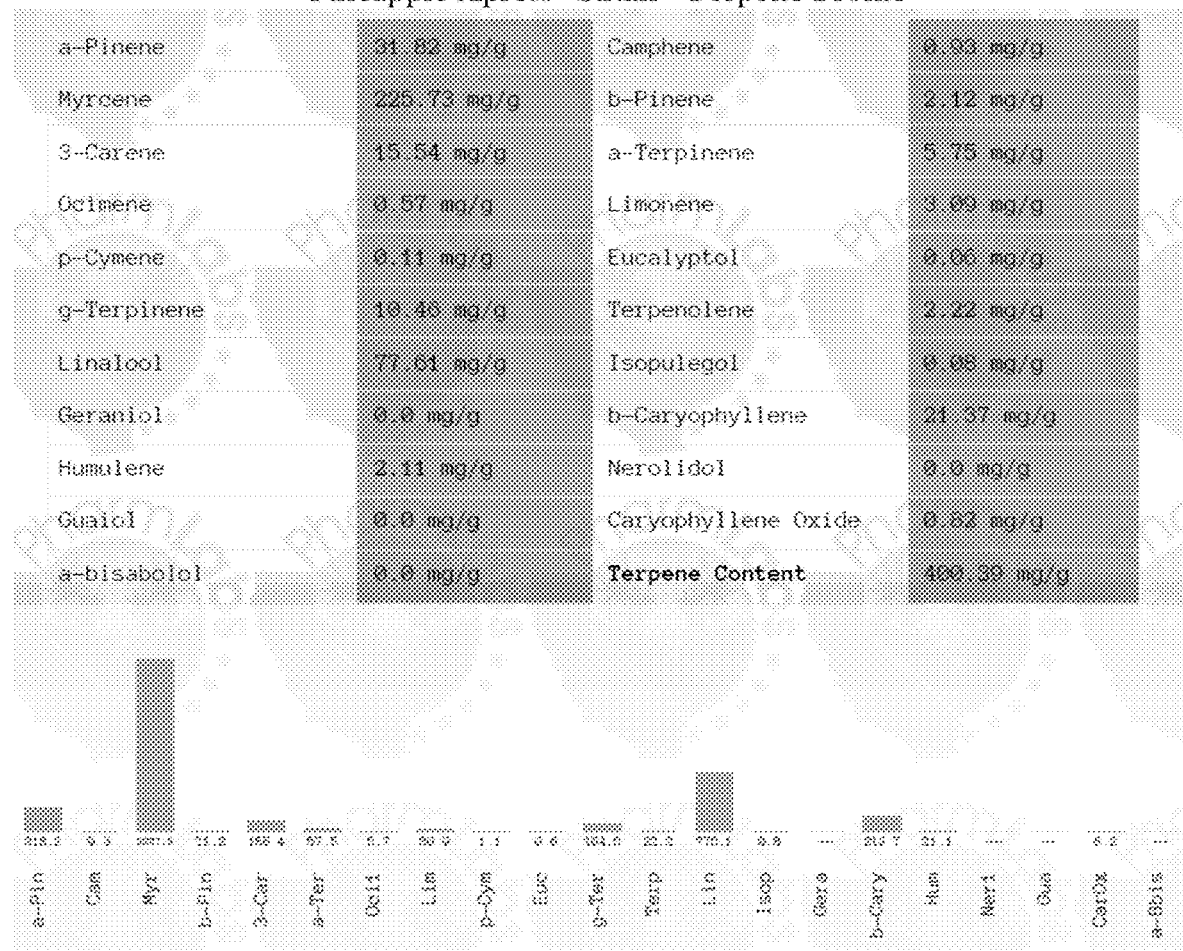
FIG. 11 shows an exemplary terpene profile of a plant sample derived from the *cannabis* strain "Pineapple Xpress." The specific amounts of each of the terpene compounds present in the sample and the total terpene content are indicated.

FIG. 11 provides an exemplary terpene profile of a plant sample derived from the *cannabis* strain "Pineapple Xpress." The specific amounts of each of the terpene compounds present in the sample and the total terpene content are indicated.

Example 13

Chemical Profiling of *Cannabis* Strain "TT JetFuel"

This Example describes the terpene profile of a sample derived from the *cannabis* strain "TT JetFuel". A concentrate from alcohol extraction was used. The analytical assay was GC/FID with Headspace Analyzer.

Figure 12:
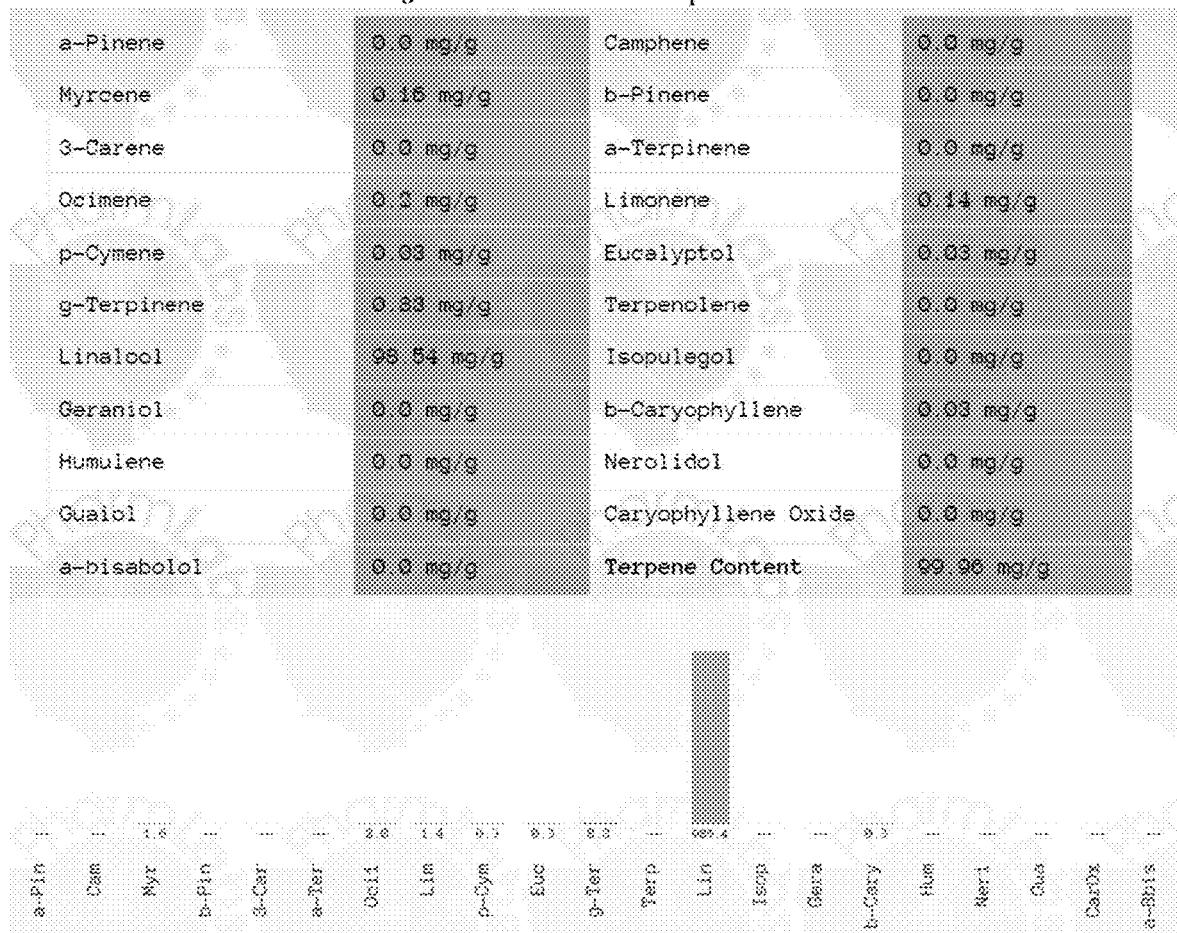
FIG. 12 shows an exemplary terpene profile of a plant sample derived from the *cannabis* strain "TT JetFuel." The specific amounts of each of the terpene compounds present in the sample and the total terpene content are indicated.

FIG. 12 provides an exemplary terpene profile of a plant sample derived from the *cannabis* strain "TT JetFuel." The specific amounts of each of the terpene compounds present in the sample and the total terpene content are indicated.

Example 15

Enriched Terpene Formulations

A number of enriched, non-naturally occurring terpene-based compositions were prepared. These formulations were derived from *cannabis* extracts through fractional distillation produced fractions, which were enriched (80% or greater) for a specific terpene. The MCT included in the formulations described in this example was derived from *cannabis* seed oil and enriched/purified to produce a fraction (80% or greater) caprylic acid. The specific terpene compounds present in each of Formulations 1-4 and their respective concentrations are described below.

FORMULATION 1: Enriched "Keep Tahoe OG". A terpene mixture with specific terpene compounds was prepared. The specific terpenes in the terpene mixture and respective concentrations are shown below.

| Compound | Amount (%) |
| --- | --- |
| Myrcene | 15.0% |
| Caryophyllene | 35.0% |
| α-Pinene | 12.0% |
| Linalool | 15.0% |
| Lime Oil | 15.0% |
| Limonene | 5.0% |

Final concentrations of the terpene mixture and enhancer (MCT) in FORMULATION 1 were 25% of terpene mixture and 75% of enhancer (MCT).

FORMULATION 2: Enriched "A Kalashnikova vTT1.0". A terpene mixture with specific terpene compounds was prepared. The specific terpenes in the terpene mixture and respective concentrations are shown below.

| Compound | Amount (%) |
| --- | --- |
| Myrcene | 45.0% |
| Caryophyllene | 20.0% |
| α-Pinene | 20.0% |
| Linalool | 10.0% |
| Lime Oil | 5.0% |

Final concentrations of the terpene mixture and enhancer (MCT) in FORMULATION 2 were 25% of terpene mixture and 75% of enhancer (MCT).

FORMULATION 3: Enriched "Terpin Gorilla". A terpene mixture with specific terpene compounds was prepared. The specific terpenes in the terpene mixture and respective concentrations are shown below.

| Compound | Amount (%) |
| --- | --- |
| Myrcene | 15% |
| Caryophyllene | 30% |
| α-Pinene | 35% |
| Lime Oil | 5% |
| β-Pinene | 15% |

Final concentrations of the terpene mixture and enhancer (MCT) in FORMULATION 3 were 50% of terpene mixture PineneMix and 50% of a *cannabis* extract.

FORMULATION 4: Enriched "ACDCvTT1.0". A terpene mixture with specific terpene compounds was prepared. The specific terpenes in the terpene mixture and respective concentrations are shown below.

| Compound | Amount (%) |
| --- | --- |
| Myrcene | 75.0% |
| Caryophyllene | 10.0% |

-continued

| Compound | Amount (%) |
|---|---|
| α-Pinene | 10.0% |
| Linalool | 5.0% |

Final concentrations of the terpene mixture and enhancer (MCT) in FORMULATION 4 were 25% of terpene mixture and 75% of enhancer (MCT). The MCT used in this formulation is caprylic MCT.

What is claimed is:

1. A non-naturally occurring composition for administration to a subject, said composition comprising one or more *cannabis* terpenes and a medium-chain triglyceride (MCT), wherein the medium chain triglyceride comprises at least one medium-chain fatty acid selected from the group consisting of caproic acid (hexanoic acid), caprylic acid (ocanoic acid), capric acid (decanoic acid), and lauric acid (dodecanoic acid), wherein the composition is a liquid, wherein the composition further comprises ethanol.

2. The composition of claim 1, wherein the total amount of terpenes in the composition is from about 0.1% to about 5%.

3. The composition of claim 1, wherein the total amount of terpenes in the composition is from about 0.1% to about 1%.

4. The composition of claim 1, wherein said composition further comprises an essential oil.

5. The composition of claim 4, wherein the amount of essential oil in the composition is from about 0.1% to about 20%.

6. The composition of claim 4, wherein the amount of essential oil in the composition is from about 5% to about 20%.

7. The composition of claim 6, wherein the ratio of the MCT amount to the amount of the at least one terpene compound is from about 100:1 to about 1:20 by volume.

8. The composition of claim 6, wherein the ratio of the MCT amount to the amount of the at least one terpene compound is about 1:1 by volume.

9. The composition of claim 1:
wherein the composition further comprises an essential oil, wherein the wherein the amount of essential oil in the composition is from about 0.1% to about 20%,
wherein the composition further comprises a flavoring ingredient,
wherein the total amount of terpenes in the composition is from about 0.1% to about 1%, and
wherein the ratio of the MCT amount to the amount of the at least one terpene compound is about 1:1 by volume.

10. The composition of claim 9, wherein the composition comprises at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpinolene, terpinene, terpineol, valencene, α-guaiene, β-guaiene, Δ-guaiene, guaiene, farnesene, α-farnesene, and β-farnesene.

11. The composition of claim 1, wherein the composition comprises at least one terpene compound selected from the group consisting of monoterpenes, diterpenes, triterpenes, hemiterpenes, sesquiterpenes, sesterterpenes, sesquarterpenes, and notisoprenoids.

12. The composition of claim 1, wherein the composition comprises at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpinolene, terpinene, terpineol, valencene, α-guaiene, β-guaiene, Δ-guaiene, guaiene, farnesene, α-farnesene, and β-farnesene.

13. The composition of claim 1, wherein the ratio of the MCT amount to the amount of the at least one terpene compound is from about 100:1 to about 1:20 by volume.

14. The composition of claim 1, wherein the ratio of the MCT amount to the amount of the at least one terpene compound is about 1:1 by volume.

15. The composition of claim 1, wherein the composition further comprises a flavoring ingredient.

16. The composition of claim 15, wherein the flavoring ingredient is selected from the group consisting of 4-hydroxy-2,5-dimethyl-3(2H)-furanone, ethyl butyrate, isoamyl acetate, propyl hexanoate, allyl hexanoate, valencene, methyl anthranilate, methyl butyrate, benzyl acetate, p-mentha-8-thiol-3-one, (1S,4S)-trans-p-menthan-8-thiol-3-one acetate, (1R,4S)-cis-p-menthan-8-thiol-3-one acetate.

17. The composition of claim 1:
wherein the composition further comprises an essential oil,
wherein the composition further comprises a flavoring ingredient, and
wherein the ratio of the MCT amount to the amount of the at least one terpene compound is about 1:1 by volume.

18. The composition of claim 17, wherein the composition comprises at least one terpene compound selected from the group consisting of 3-carene, α-bisabolol, β-caryophyllene, bisabolol, borneol, camphene, carene, caryophyllene, caryophyllene oxide, citronellol, eucalyptol, fenchol, geraniol, γ-terpinene, guaiol, humulene, isopulegol, limonene, linalool, menthol, myrcene, ocimene, p-cymene, phellandrene, phytol, α-pinene, β-pinene, terpinolene, terpinene, terpineol, valencene, α-guaiene, β-guaiene, Δ-guaiene, guaiene, farnesene, α-farnesene, and β-farnesene.

19. The composition of claim 1, wherein the MCT comprises at least one medium-chain fatty acid having an aliphatic tail of 6-12 carbon atoms.

20. The composition of claim 1, wherein the medium-chain fatty acid comprises caprylic acid.

21. The composition of claim 1, wherein the ratio of the MCT amount to the amount of the at least one terpene compound is from about 100:1 to about 3:1 by volume.

22. The composition of claim 1, wherein the one or more *cannabis* terpenes comprise at least one terpene compound selected from the group consisting of caryophyllene, limonene, linalool, myrcene, α-pinene, and β-pinene.

23. The composition of claim 1, wherein the composition further comprises a plurality of chemical compounds which are known to occur in a *cannabis* strain, wherein the amounts of said plurality of chemical compounds, including said one or more *cannabis* terpenes, with respect to one another in said composition, are about the same as the amounts of said plurality of chemical compounds with respect to one another in said *cannabis* strain.

24. The composition of claim 23, wherein the plurality of chemical compounds are selected from the group consisting of terpenes, terpenoids, cannabinoids, nitrogenous compounds, amino acids, proteins, glycoproteins, enzymes, sugars and related compounds, hydrocarbons, simple alcohols, aldehydes, ketones, simple acids, fatty acids, simple esters, lactones, steroids, non-cannabinoid phenols, flavonoids, vitamins, pigments, and other elements.

25. The composition of claim 23, wherein said plurality of chemical compounds comprises one or more cannabinoid compound.

26. The composition of claim 25, wherein the one or more cannabinoid compounds are selected from the group consisting of cannabinol (CBN), cannabinolic acid (CBNA), Δ(9)-tetrahydrocannabinol (Δ(9)-THC), Δ(9)-tetrahydrocannabinolic acid (Δ(9)-THCA), Δ(9)-cannabidiol (Δ(9)-CBD), Δ(9)-cannabidiolic acid (Δ(9)-CBDA), Δ(8)-tetrahydrocannabinol (Δ(8)-THC), Δ(8)-tetrahydrocannabinolic acid (Δ(8)-THCA), Δ(8)-cannabidiol (Δ(8)-CBD), Δ(8)-cannabidiolic acid (Δ(8)-CBDA), Δ(9)-tetrahydrocannabivarin (Δ(9)-THV), cannabigerol (CBG), cannabigerolic acid (CBGA), cannabichromene (CBC), cannabichromenic acid (CBCA), cannabicyclol (CBL), cannabicyclolic acid (CBLA), and active analogues and derivatives of any one thereof.

27. The composition of claim 26, wherein the one or more cannabinoid compounds are selected from the group consisting of Δ(9)-tetrahydrocannabinolic acid (Δ(9)-THCA), Δ(9)-cannabidiolic acid (Δ(9)-CBDA), and active analogues and derivatives of any one thereof.

* * * * *